United States Patent
Melis

(10) Patent No.: US 7,947,478 B2
(45) Date of Patent: May 24, 2011

(54) SHORT CHAIN VOLATILE HYDROCARBON PRODUCTION USING GENETICALLY ENGINEERED MICROALGAE, CYANOBACTERIA OR BACTERIA

(75) Inventor: Anastasios Melis, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 245 days.

(21) Appl. No.: 11/770,412

(22) Filed: Jun. 28, 2007

(65) Prior Publication Data

US 2008/0038805 A1    Feb. 14, 2008

Related U.S. Application Data

(60) Provisional application No. 60/806,244, filed on Jun. 29, 2006.

(51) Int. Cl.
*C12P 5/02*     (2006.01)
*C12N 1/21*     (2006.01)
*C12N 1/13*     (2006.01)

(52) U.S. Cl. .................. 435/167; 435/252.3; 435/257.2

(58) Field of Classification Search .......................... None
See application file for complete search history.

(56) References Cited

U.S. PATENT DOCUMENTS

| | | | |
|---|---|---|---|
| 5,849,970 | A | 12/1998 | Fall et al. |
| 6,916,972 | B2 | 7/2005 | Falco et al. |
| 2002/0119546 | A1 | 8/2002 | Falco et al. |
| 2003/0041338 | A1 | 2/2003 | Falco et al. |
| 2003/0219798 | A1 | 11/2003 | Gokarn et al. |
| 2005/0183163 | A1 | 8/2005 | Falco et al. |
| 2005/0183164 | A1 | 8/2005 | Falco et al. |

FOREIGN PATENT DOCUMENTS

| | | |
|---|---|---|
| WO | WO 98/25550 A2 | 7/1997 |
| WO | WO 98/02550 | 1/1998 |
| WO | WO 02/086094 A2 | 10/2002 |
| WO | WO 2007/140339 | 12/2007 |
| WO | WO 2008/137092 A2 | 11/2008 |

OTHER PUBLICATIONS

Steve Davidson (ECOS Magazine. Oct.-Dec. 2003; 117: 10-12).*
Stevens et al. (J. Physiol. 1997; 33: 713-722).*
Sasaki et al (FEBS Letters 579. 2005; 2514-2518).*
Broadgate, W.J. et al.; "Isoprene and other non-methane hydrocarbons from seaweeds: a source of reactive hydrocarbons to the atmosphere"; 2004, *Marine Chemistry*, vol. 88, pp. 61-73.
Davidson, Steve; "Light Factories"; 2003, *ECOS*, vol. 117, pp. 10-12.
Logan, Barry A. et al.; "Biochemistry and physiology of foliar isoprene production"; 2000, *Trends in Plant Science*, vol. 5, No. 11, pp. 477-481.
McKay, W.A. et al.; "Emissions of Hydrocarbons from Marine Phytoplankton—some results from controlled Laboratory Experiments"; 1996, *Atmospheric Environment*, vol. 30, No. 14, pp. 2583-2593.
Miller, Barbara et al.; "First isolation of an isoprene synthase gene from popular and successful expression of the gene in *Escherichia coli*"; 2001, *Planta*, vol. 213, pp. 483-487.
Sasaki, Kanako et al.; "Gene expression and characterization of isoprene synthase from *Populus alba*"; 2005, FEBS Letters, vol. 579, pp. 2514-2518.
Sasaki, Kanako et al.; "Plants Utilize Isoprene Emission as a Thermotolerance Mechanism"; 2007, *Plant Cell Physiol.*, vol. 48, No. 9, pp. 1254-1262.
Sharkey, Thomas D. et al.; "Evolution of the Isoprene Biosynthetic Pathway in Kudzu"; 2005, *Plant Physiology*, vol. 137, pp. 700-712. GenBank accession No. AM410988, 2 pages.
Davidson, S. (Oct.-Dec. 2003). "Light Factories," *ECOS*, published by CSIRO, 117:10-12; also available at http://www.publish.csiro.au/?act=view_file&file_id=EC117p10.pdf, last visited on Apr. 7, 2008.
Miller, B et al. (Jul. 2001). "First Isolation of an Isoprene Synthase Gene from Poplar and Successful Expression of the Gene in *Escherichia coli*," Planta, Fraunhofer Institut fur Atmospharische Umweltforschung, Germany, 213(3):483-487.
Sasaki, K. et al. "Gene Expression and Characterization of Isoprene Synthase from *Populus alba*," *FEBS Letters*, Laboratory of Plant Gene Expression, Research Institute for Sustainable Humanosphere, Kyoto University, Gokasho, Japan, 579(11):2514-2518, (2005).
Sharkey, T. D. et al. (Feb. 2005). "Evolution of the Isoprene Biosynthetic Pathway in Kudzu," *Plant Physiology*, Department of Botany, University of Wisconsin, Madison, Wisconsin and Protemix Corporation, University of Auckland, Auckland City, New Zealand, 137:700:712; also available at http://www.plantphysiol.org/cgi/reprint/137/2/700.pdf, last visited on Apr. 7, 2008.
Ladygina, N. et al.; "A review on microbial synthesis of hydrocarbons"; 2006, *Process Biochemistry*, vol. 41, pp. 1001-1014.
Lindberg, P. et al.; "Engineering a platform for photosynthetic isoprene production in cyanobacteria, using synechocystis as the model organism"; 2010, *Metabolic Engineering*, vol. 12, pp. 70-79.
Miller, Barbara; "Erstmalige Isolierung eines Isoprensynthase-Gens und heterologe Expression des aus der Pappel stammenden Gens sowie Charakterisierung der Eingangsgene des Mevalonat-unabhangigen Isoprenoidbiosyntheseseweges aus dem Cyanobakterium Synechococcus"; 2003, Internet Citation, URL:http://kups.ub.uni-koeln.de/volltexte/2003/883/pdf/millerbarbara.pdf>, pp. 1-2.

* cited by examiner

*Primary Examiner* — Scott Long
(74) *Attorney, Agent, or Firm* — Kilpatrick Townsend & Stockton LLP

(57) ABSTRACT

The present invention provides methods and compositions for producing isoprene hydrocarbons from microalgae, cyanobacteria, and photosynthetic and non-photosynthetic bacteria.

8 Claims, 14 Drawing Sheets

Abbreviations used:
GA-3-P = glyceraldehydes-3-phosphate
IPP = isopentenyl pyrophosphate
DMAPP = dimethylallyl- pyrophosphate

A

B

Expected size of His-IspS is 65 kD (asterisk)

Figure 13

CLUSTAL W (1.83) multiple sequence alignments of known IspS proteins
   The putative chloroplast transit peptide cpTP is shown by underlined sequences;
   All Cys amino acids are in large, highlighted font, including conservative Ser
substitutions

```
alba         MATELLCLHRPISLTHKLFRNPLP--------KVIQATPLTLKLRCSVSTENVSFTETET  52
tremuloides  MATELLCLHRPISLTHKLFRNPLP--------KVIQATPLTLKLRCSVSTENVSFSETET  52
nigra        MATELLCLHRPISLTHKLFRNPLP--------KVIQATPLTLKLRCSVSTENVSFTETET  52
kudzu        MATNLLCLSNKLSSPTPTPSTRFPQSKNFITQKTSLANPKPWRVICATSSQFTQITEHN-  59
             ***:****  .:*  .      .:*     *.  *.* . :: *:..*::  ..::* :

alba         EARRSANYEPNSWDYDYLLSSDTDESIEVYKDKAKKLEAEVRREINNEKAEFLTLLELID 112
tremuloides  ETRRSANYEPNSWDYDYLLSSDTDESIEVHKDKAKKLEAEVRREINNEKAEFLTLLELID 112
nigra        ETRRSANYEPNSWDYDYLLSSDTDESIEVYKDKAKKLEAEVRREINNEKAEFLTLPELID 112
kudzu        -SRRSANYQPNLWNFEFLQSLENDLKVEKLEEKATKLEEEVRCMINRVDTQPLSLLELID 118
              :****: *:::*  * :.* .:*  ::.* * ..::: *:* **** alba         NVQRLGLGYRFESDIRGALDRFVSSGGFDAVTKTSLHGTALSFRLLRQHGFEVSQEAFSG 172
tremuloides  NVQRLGLGYRFESDIRRALDRFVSSGGFDGVTKTSLHGTALSFRLLRQHGFEVSQEAFSG 172
nigra        NVQRLGLGYRFESDIRRALDRFVSSGGFDAVTKTSLHATALSFRLLRQHGFEVSQEAFSG 172
kudzu        DVQRLGLTYKFEKDIIKALENIVLLD-ENKKNKSDLHATALSFRLLRQHGFEVSQDVFER 177
             :****** *:**.**  **:.:*   .  :  .*:.**.****************::.*.

alba         FKDQNGNFLENLKEDIKAILSLYEASFLALEGENILDEAKVFAISHLKELSEEKIGKELA 232
tremuloides  FKDQNGNFLENLKEDIKAILSLYEASFLALEGENILDEAKVFAISHLKELSEEKIGKELA 232
nigra        FKDQNGNFLKNLKEDIKAILSLYEASFLALEGENILDEAKVFAISHLKELSEEKIGKDLA 232
kudzu        FKDKEGGFSGELKGDVQGLLSLYEASYLGFEGENLLEEARTFSITHLKNNLKEGINTKVA 237
             ***::*.:*   :** *::.:*******.*:.:****:*:**:.*:*:***:   :* *....:* alba         EQVNHALELPLHRRTQRLEAVWSIEAYRKKEDANQVLLELAILDYNMIQSVYQRDLRETS 292
tremuloides  EQVSHALELPLHRRTQRLEAVWSIEAYRKKEDANQVLLELAILDYNMIQSVYQRDLRETS 292
nigra        EQVNHALELPLHRRTQRLEAVWSIEAYRKKEDADQVLLELAILDYNMIQSVYQRDLRETS 292
kudzu        EQVSHALELPYHQRLHRLEARWFLDKYEPKEPHHQLLLELAKLDFNMVQTLHQKELQDLS 297
             *.****  *:*  :**** *  ::  *.  .*:*** :**:*:::*::  * alba         RWWRRVGLATKLHFARDRLIESFYWAVGVAFEPQYSDCRNSVAKMFSFVTIIDDIYDVYG 352
tremuloides  RWWRRVGLATKLHFARDRLIESFYWAVGVAFEPQYSDCRNSVAKMFSFVTIIDDIYDVYG 352
nigra        RWWRRVGLATKLHFARDRLIESFYWAVGVAFEPQYSDCRNSVAKMFSFVTIIDDIYDVYG 352
kudzu        RWWTEMGLASKLDFVRDRLMEVYFWALGMAPDPQFGECRKAVTKMFGLVTIIDDVYDVYG 357
             *  .:*:**.*.****:* .*:**:*  .::.::**.*:* .:** :*** alba         TLDELELFTDAVERWDVNAINDLPDYMKLCFLALYNTINEIAYDNLKDKGENILPYLTKA 412
tremuloides  TLDELELFTDAVERWDVNAINDLPDYMKLCFLALYNTINEIAYDNLKDKGENILPYLTKA 412
nigra        TLDELELFTDAVERWDVNAIDDLPDYMKLCFLALYNTINEIAYDNLKDKGENILPYLTKA 412
kudzu        TLDELQLFTDAVERWDVNAINTLPDYMKLCFLALYNTVNDTSYSILKEKGHNNLSYLTKS 417
             *****:**************:. **********:*. :*. **:**.* *.****:

alba         WADLCNAFLQEAKWLYNKSTPTFDDYFGNAWKSSSGPLQLVFAYFAVVQN---IKKEEIE 469
tremuloides  WADLCNAFLQEAKWLYNKSTPTFDDYFGNAWKSSSGPLQLIFAYFAVVQN---IKKEEIE 469
nigra        WADLCNAFLQEAKWLYNKSTPTFDEYFGNAWKSSSGPLQLVFAYFAVVQN---IKKEEID 469
kudzu        WRELCKAFLQEAKWSNNKIIPAFSKYLENASVSSSGVALLAPSYFSVCQQQEDISDHALR 477
             * :**:******** ** *:*..*: ** ****  * :**:* *:   *... :

alba         NLQKYHDTISRPSHIFRLCNDLASASAEIARGETANSVSCYMR-TKGISEELATESVMNL 528
tremuloides  NLQKYHDIISRPSHIFRLCNDLASASAEIARGETANSVSCYMR-TKGISEELATESVMNL 528
nigra        NLQKYHDIISRPSHIFRLCNDLASASAEIARGETANSVSCYMR-TKGISEELATESVMNL 528
kudzu        SLTDFHGLVRSSCVIFRLCNDLATSAAELERGETTNSIISYMHENDGTSEEQAREELRKL 537
             .*  ..:*. :    ..  **********:::**: ****:  .**:   ..: *** * *..* :*
```

Figure 13-continued

```
alba        IDETWKKMNKEKLGGS-LFAKPFVETAINLARQSHCTYHNGDAHTSPDELTRKRVLSVIT 587
tremuloi    IDETWKKMNKEKLGGS-LFAKPFVETAINLARQSHCTYHNGDAHTSPDELTRKRVLSVIT 587
nigra       IDETWKKMNKEKLGGS-LFAKPFVETAINLARQSHCTYHNGDAHTSPDELTRKRVLSVIT 587
kudzu       IDAEWKKMNRERVSDSTLLPKAFMEIAVNMARVSHCTYQYGDGLGRPDYATENRIKLLLI 597
            **  *****:*:..* *:.*.*:* *:*:** *****: **.    **  *.:*:   ::

alba        EPILPFER--- 595
tremuloi    EPILPFER--- 595
nigra       EPILPFER--- 595
kudzu       DPFPINQLMYV 608
            :*:    :
```

SEQUENCE LISTING

<160> NUMBER OF SEQ ID NOS: 13

<210> SEQ ID NO 1
<211> LENGTH: 1788
<212> TYPE: DNA
<213> ORGANISM: Populus alba
<220> FEATURE:
<223> OTHER INFORMATION: white poplar isoprene synthase (IspS) cDNA

<400> SEQUENCE: 1

```
atggcaactg aattattgtg cttgcaccgt ccaatctcac tgacacacaa acttttcaga     60
aatcccttac ctaaagtcat ccaggccact cccttaactt tgaaactcag atgttctgta    120
agcacagaaa acgtcagctt cacagaaaca gaaacagaag ccagacggtc tgccaattat    180
gaaccaaata gctgggatta tgattatttg ctgtcttcag acactgacga atcgattgag    240
gtatacaaag acaaggccaa aaagctggag gctgaggtga aagagagat taacaatgaa    300
aaggcagagt ttttgactct gcttgaactg atagataatg tccaaaggtt aggattgggt    360
taccggttcg agagtgacat aaggggagcc cttgatagat ttgtttcttc aggaggattt    420
gatgctgtta caaaaactag ccttcatggt actgctctta gcttcaggct tctcagacag    480
catggttttg aggtctctca agaagcgttc agtggattca aggatcaaaa tggcaatttc    540
ttggaaaacc ttaaggagga catcaaggca atactaagcc tatatgaagc ttcatttctt    600
gcattagaag gagaaaatat cttggatgag gccaaggtgt ttgcaatatc acatctaaaa    660
gagctcagcg aagaaaagat tggaaaagag ctggccgaac aggtgaatca tgcattggag    720
cttccattgc atcgcaggac gcaaagacta gaagctgttt ggagcattga agcataccgt    780
aaaaaggaag atgcaaatca agtactgcta gaacttgcta tattggacta caacatgatt    840
caatcagtat accaaagaga tcttcgcgag acatcaaggt ggtggaggcg agtgggtctt    900
gcaacaaagt tgcatttgc tagagacagg ttaattgaaa gcttttactg gcagttggaa    960
gttgcgttcg agcctcaata cagtgattgc cgtaattcag tagcaaaaat gttttcattt   1020
gtaacaatca ttgatgatat ctatgatgtt tatggtactc tggacgagtt ggagctattt   1080
acagatgctg ttgagagatg ggatgttaat gccatcaatg atcttccgga ttatatgaag   1140
ctctgcttcc tagctctcta caacactatc aatgagtag cttatgacaa tctgaaggac   1200
aaggggaaa acattcttcc atacctaaca aaagcgtggg cagatttatg caatgcattc   1260
ctacaagaag caaatggtt gtacaataag tccacaccaa catttgatga ctatttcgga   1320
aatgcatgga atcatcctc agggcctctt caactagttt ttgcctactt tgccgtggtt   1380
caaaacatca agaaagagga aattgaaaac ttacaaaagt atcatgatac catcagtagg   1440
ccttcccaca tctttcgtct ttgcaacgac ctggcttcag catcggctga gatagcgaga   1500
ggtgaaacag cgaattctgt atcatgctac atgcgtacaa aaggcattc tgaggagctt   1560
gctactgaat ccgtaatgaa cttgatcgac gaaacctgga aaagatgaa caaagaaaag   1620
cttggtggct ctttgtttgc aaaaccttt gtcgaaacag ctattaacct tgcacggcaa   1680
tcccattgca cttatcataa cggagatgcg catacttcac cagacgagct aactaggaaa   1740
cgtgtcctgt cagtaatcac agagcctatt ctacccttg agagataa                 1788
```

<210> SEQ ID NO 2
<211> LENGTH: 595
<212> TYPE: PRT
<213> ORGANISM: Populus alba
<220> FEATURE:

```
<223> OTHER INFORMATION: white poplar isoprene synthase (IspS)
<220> FEATURE:
<221> NAME/KEY: PEPTIDE
<222> LOCATION: (1)..(37)
<223> OTHER INFORMATION: chloroplast transit peptide

<400> SEQUENCE: 2
```

| | | | | | | | | | | | | | | |
|---|---|---|---|---|---|---|---|---|---|---|---|---|---|---|
|Met|Ala|Thr|Glu|Leu|Leu|Cys|Leu|His|Arg|Pro|Ile|Ser|Leu|Thr|His|
|1| | | |5| | | | |10| | | | |15| |

Lys Leu Phe Arg Asn Pro Leu Pro Lys Val Ile Gln Ala Thr Pro Leu
                20                  25                  30

Thr Leu Lys Leu Arg Cys Ser Val Ser Thr Glu Asn Val Ser Phe Thr
            35                  40                  45

Glu Thr Glu Thr Glu Ala Arg Arg Ser Ala Asn Tyr Glu Pro Asn Ser
        50                  55                  60

Trp Asp Tyr Asp Tyr Leu Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
                85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Gly Ala Leu Asp Arg Phe Val Ser Ser Gly Gly Phe Asp Ala Val Thr
        130                 135                 140

Lys Thr Ser Leu His Gly Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Lys Val Phe Ala Ile Ser His Leu Lys Glu Leu Ser Glu
    210                 215                 220

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
            260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
    290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asn Asp Leu Pro Asp Tyr Met Lys Leu Cys Phe Leu
    370                 375                 380

```
Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
            405                 410                 415

Cys Asn Ala Phe Leu Gln Glu Ala Lys Trp Leu Tyr Asn Lys Ser Thr
        420                 425                 430

Pro Thr Phe Asp Asp Tyr Phe Gly Asn Ala Trp Lys Ser Ser Ser Gly
    435                 440                 445

Pro Leu Gln Leu Val Phe Ala Tyr Phe Ala Val Val Gln Asn Ile Lys
450                 455                 460

Lys Glu Glu Ile Glu Asn Leu Gln Lys Tyr His Asp Thr Ile Ser Arg
465                 470                 475                 480

Pro Ser His Ile Phe Arg Leu Cys Asn Asp Leu Ala Ser Ala Ser Ala
            485                 490                 495

Glu Ile Ala Arg Gly Glu Thr Ala Asn Ser Val Ser Cys Tyr Met Arg
        500                 505                 510

Thr Lys Gly Ile Ser Glu Glu Leu Ala Thr Glu Ser Val Met Asn Leu
    515                 520                 525

Ile Asp Glu Thr Trp Lys Lys Met Asn Lys Glu Lys Leu Gly Gly Ser
530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
            565                 570                 575

Leu Thr Arg Lys Arg Val Leu Ser Val Ile Thr Glu Pro Ile Leu Pro
        580                 585                 590

Phe Glu Arg
        595

<210> SEQ ID NO 3
<211> LENGTH: 1776
<212> TYPE: DNA
<213> ORGANISM: Artificial Sequence
<220> FEATURE:
<223> OTHER INFORMATION: Description of Artificial Sequence:
      codon-adjusted synthetic DNA construct for expression of Populus
      alba IspS gene with chloroplast targeting sequence omitted and
      hemagglutinin (HA) epitope tag in microalga Chlamydomonas
      reinhardtii (Cr-IspS)
<220> FEATURE:
<221> NAME/KEY: gene
<222> LOCATION: (100)..(1776)
<223> OTHER INFORMATION: Populus alba IspS gene with chloroplast
      targeting sequence omitted codon-optimized for expression in
      microalga Chlamydomonas reinhardtii chloroplast (Cr-IspS)

<400> SEQUENCE: 3
atgtatcctt atgatgttcc agactacgca ggttatcctt atgatgtacc agactatgca      60
ggttatcctt acgatgtacc tgattacgct ggtccatggt gttctgttag tactgaaaat     120
gtttcattta ctgaaacaga aacagaagca cgtagatcag caaattatga gccaaatagt     180
tgggattatg actatttatt atctagtgat acagatgaat ctattgaagt atataaagat     240
aaagcaaaaa aattagaagc agaagtacgt cgtgaaatta ataacgaaaa agcagaattt     300
cttactttat tagaattaat tgataatgta caacgtttag gtttaggtta tcgttttgaa     360
tcagacattc gtggtgcatt agatcgtttt gtatcaagtg gtggttttga tgctgttaca     420
aaaactagtt tacatggtac tgctttaagt tttcgtttac ttcgtcaaca tggttttgaa     480
gtaagtcaag aagcttttt ctggttttaaa gatcaaaatg gtaatttctt agaaaattta     540
```

-continued

```
aaagaagata ttaaagctat tttaagttta tacgaagcat catttttagc tttagaaggt    600
gaaatatttt tagatgaagc taaagtattt gctatttctc acttaaaaga attatcagaa    660
gaaaaaattg gtaaagaatt agctgaacaa gtaaaccatg cattagaatt accattacat    720
cgtcgtacac aacgtttaga agcagtttgg tctattgaag cttatcgtaa aaagaagat    780
gctaatcaag ttttattaga attagcaatt ttagattata atatgattca atcagtatac    840
caacgtgatt tacgtgaaac aagtcgttgg tggcgtcgtg taggtttagc tactaaatta    900
cattttgctc gtgatcgttt aattgaaagt ttttattggg cagttggtgt agcttttgaa    960
ccacaatatt cagattgtcg taattcagtt gcaaaaatgt tttcatttgt aactattatt   1020
gatgatattt atgatgttta cggtacatta gatgaattag aattattcac tgatgcagta   1080
gaacgttggg atgttaatgc tattaatgat ttaccagatt atatgaaatt atgttttctt   1140
gctttatata acactattaa tgaaattgct tatgataact aaaagataa aggtgaaaat   1200
attttaccat atttaacaaa agcttgggct gattatgta atgcttttttt acaagaagct   1260
aaatggttat ataataaatc aacaccaaca tttgatgatt attttggtaa tgcttggaaa   1320
agttcatctg gtccattaca attagttttt gcttatttttg ctgttgttca aaatattaaa   1380
aaagaagaaa ttgaaaattt acaaaaatat catgatacaa tttcacgtcc atcacatatt   1440
tttcgtttat gtaatgattt agcttcagct tcagctgaaa ttgcacgtgg tgaaacagca   1500
aattcagttt catgttatat gcgtacaaaa ggtatttctg aagaattagc tacagaatca   1560
gttatgaatt taattgatga acatggaaaa aaaatgaata agaaaaatt aggtggttct   1620
ttatttgcta aaccatttgt tgaaactgct attaatttag cacgtcaatc acattgtact   1680
tatcataatg gtgatgctca tacatccacca gatgaattaa cacgtaaacg tgttttatca   1740
gttattacag aaccaatttt accatttgaa cgttaa                             1776
```

<210> SEQ ID NO 4
<211> LENGTH: 591
<212> TYPE: PRT
<213> ORGANISM: Artificial Sequence
<220> FEATURE:
<223> OTHER INFORMATION: Description of Artificial Sequence:Populus
      alba isoprene synthase (IspS) with chloroplast targeting sequence
      omitted and hemagglutinin (HA) epitope tag fusion protein for
      expression in microalga Chlamydomonas reinhardtii chloroplast
<220> FEATURE:
<221> NAME/KEY: PEPTIDE
<222> LOCATION: (2)..(10)
<223> OTHER INFORMATION: hemagglutinin (HA) epitope tag peptide
<220> FEATURE:
<221> NAME/KEY: PEPTIDE
<222> LOCATION: (12)..(20)
<223> OTHER INFORMATION: hemagglutinin (HA) epitope tag peptide
<220> FEATURE:
<221> NAME/KEY: PEPTIDE
<222> LOCATION: (22)..(30)
<223> OTHER INFORMATION: hemagglutinin (HA) epitope tag peptide
<220> FEATURE:
<221> NAME/KEY: PEPTIDE
<222> LOCATION: (34)..(591)
<223> OTHER INFORMATION: Populus alba isoprene synthase (IspS) with
      chloroplast targeting sequence omitted

<400> SEQUENCE: 4

```
Met Tyr Pro Tyr Asp Val Pro Asp Tyr Ala Gly Tyr Pro Tyr Asp Val
 1               5                  10                  15

Pro Asp Tyr Ala Gly Tyr Pro Tyr Asp Val Pro Asp Tyr Ala Gly Pro
                20                  25                  30

Trp Cys Ser Val Ser Thr Glu Asn Val Ser Phe Thr Glu Thr Glu Thr
            35                  40                  45
```

Glu Ala Arg Arg Ser Ala Asn Tyr Glu Pro Asn Ser Trp Asp Tyr Asp
            50                  55                  60

Tyr Leu Leu Ser Ser Asp Thr Asp Glu Ser Ile Glu Val Tyr Lys Asp
65                  70                  75                  80

Lys Ala Lys Lys Leu Glu Ala Glu Val Arg Arg Glu Ile Asn Asn Glu
                85                  90                  95

Lys Ala Glu Phe Leu Thr Leu Leu Glu Leu Ile Asp Asn Val Gln Arg
            100                 105                 110

Leu Gly Leu Gly Tyr Arg Phe Glu Ser Asp Ile Arg Gly Ala Leu Asp
            115                 120                 125

Arg Phe Val Ser Ser Gly Gly Phe Asp Ala Val Thr Lys Thr Ser Leu
130                 135                 140

His Gly Thr Ala Leu Ser Phe Arg Leu Leu Arg Gln His Gly Phe Glu
145                 150                 155                 160

Val Ser Gln Glu Ala Phe Ser Gly Phe Lys Asp Gln Asn Gly Asn Phe
                165                 170                 175

Leu Glu Asn Leu Lys Glu Asp Ile Lys Ala Ile Leu Ser Leu Tyr Glu
            180                 185                 190

Ala Ser Phe Leu Ala Leu Glu Gly Glu Asn Ile Leu Asp Glu Ala Lys
            195                 200                 205

Val Phe Ala Ile Ser His Leu Lys Glu Leu Ser Glu Glu Lys Ile Gly
210                 215                 220

Lys Glu Leu Ala Glu Gln Val Asn His Ala Leu Glu Leu Pro Leu His
225                 230                 235                 240

Arg Arg Thr Gln Arg Leu Glu Ala Val Trp Ser Ile Glu Ala Tyr Arg
                245                 250                 255

Lys Lys Glu Asp Ala Asn Gln Val Leu Leu Glu Leu Ala Ile Leu Asp
            260                 265                 270

Tyr Asn Met Ile Gln Ser Val Tyr Gln Arg Asp Leu Arg Glu Thr Ser
            275                 280                 285

Arg Trp Trp Arg Arg Val Gly Leu Ala Thr Lys Leu His Phe Ala Arg
290                 295                 300

Asp Arg Leu Ile Glu Ser Phe Tyr Trp Ala Val Gly Val Ala Phe Glu
305                 310                 315                 320

Pro Gln Tyr Ser Asp Cys Arg Asn Ser Val Ala Lys Met Phe Ser Phe
                325                 330                 335

Val Thr Ile Ile Asp Asp Ile Tyr Asp Val Tyr Gly Thr Leu Asp Glu
            340                 345                 350

Leu Glu Leu Phe Thr Asp Ala Val Glu Arg Trp Asp Val Asn Ala Ile
            355                 360                 365

Asn Asp Leu Pro Asp Tyr Met Lys Leu Cys Phe Leu Ala Leu Tyr Asn
370                 375                 380

Thr Ile Asn Glu Ile Ala Tyr Asp Asn Leu Lys Asp Lys Gly Glu Asn
385                 390                 395                 400

Ile Leu Pro Tyr Leu Thr Lys Ala Trp Ala Asp Leu Cys Asn Ala Phe
                405                 410                 415

Leu Gln Glu Ala Lys Trp Leu Tyr Asn Lys Ser Thr Pro Thr Phe Asp
            420                 425                 430

Asp Tyr Phe Gly Asn Ala Trp Lys Ser Ser Gly Pro Leu Gln Leu
            435                 440                 445

Val Phe Ala Tyr Phe Ala Val Val Gln Asn Ile Lys Lys Glu Glu Ile
450                 455                 460

Glu Asn Leu Gln Lys Tyr His Asp Thr Ile Ser Arg Pro Ser His Ile

```
                465                 470                 475                 480
    Phe Arg Leu Cys Asn Asp Leu Ala Ser Ala Ser Ala Glu Ile Ala Arg
                        485                 490                 495
    Gly Glu Thr Ala Asn Ser Val Ser Cys Tyr Met Arg Thr Lys Gly Ile
                500                 505                 510
    Ser Glu Glu Leu Ala Thr Glu Ser Val Met Asn Leu Ile Asp Glu Thr
            515                 520                 525
    Trp Lys Lys Met Asn Lys Glu Lys Leu Gly Gly Ser Leu Phe Ala Lys
            530                 535                 540
    Pro Phe Val Glu Thr Ala Ile Asn Leu Ala Arg Gln Ser His Cys Thr
    545                 550                 555                 560
    Tyr His Asn Gly Asp Ala His Thr Ser Pro Asp Glu Leu Thr Arg Lys
                    565                 570                 575
    Arg Val Leu Ser Val Ile Thr Glu Pro Ile Leu Pro Phe Glu Arg
                580                 585                 590

<210> SEQ ID NO 5
<211> LENGTH: 3965
<212> TYPE: DNA
<213> ORGANISM: Artificial Sequence
<220> FEATURE:
<223> OTHER INFORMATION: Description of Artificial Sequence:
      codon-optimized synthetic DNA construct for expression of Populus
      alba IspS gene with chloroplast targeting sequence omitted in
      Synechocystis sp. cyanobacteria (Ss-IspS) with beta-lactamase
      gene (reverse complement)
<220> FEATURE:
<221> NAME/KEY: gene
<222> LOCATION: Complement(1084)..(1944)
<223> OTHER INFORMATION: beta-lactamase gene (reverse complement)
<220> FEATURE:
<221> NAME/KEY: gene
<222> LOCATION: (2256)..(3890)
<223> OTHER INFORMATION: Populus alba IspS gene with chloroplast
      targeting sequence omitted codon-optimized for expression in
      Synechocystis sp. cyanobacteria (Ss-IspS)

<400> SEQUENCE: 5
aaaaagcatt gctcatcaat tgttgcaac gaacaggtca ctatcagtca aaataaaatc        60
attatttaaa aggggcccga gcttaagact ggccgtcgtt ttacaacaca gaaagagttt      120
gtagaaacgc aaaaaggcca tccgtcaggg gccttctgct tagtttgatg cctggcagtt      180
ccctactctc gccttccgct tcctcgctca ctgactcgct gcgctcggtc gttcggctgc      240
ggcgagcggt atcagctcac tcaaaggcgg taatacggtt atccacagaa tcaggggata      300
acgcaggaaa gaacatgtga gcaaaaggcc agcaaaaggc caggaaccgt aaaaaggccg      360
cgttgctggc gttttccat aggctccgcc cccctgacga gcatcacaaa aatcgacgct      420
caagtcagag gtggcgaaac ccgacaggac tataaagata ccaggcgttt ccccctggaa      480
gctccctcgt gcgctctcct gttccgaccc tgccgcttac cggatacctg tccgcctttc      540
tcccttcggg aagcgtggcg ctttctcata gctcacgctg taggtatctc agttcggtgt      600
aggtcgttcg ctccaagctg ggctgtgtgc acgaaccccc cgttcagccc gaccgctgcg      660
ccttatccgg taactatcgt cttgagtcca acccggtaag acacgactta tcgccactgg      720
cagcagccac tggtaacagg attagcagag cgaggtatgt aggcggtgct acagagttct      780
tgaagtggtg gcctaactac ggctacacta gaagaacagt atttggtatc tgcgctctgc      840
tgaagccagt taccttcgga aaaagagttg gtagctcttg atccggcaaa caaaccaccg      900
ctggtagcgg tggtttttt gtttgcaagc agcagattac gcgcagaaaa aaaggatctc      960
aagaagatcc tttgatcttt tctacggggt ctgacgctca gtggaacgac gcgcgcgtaa     1020
```

```
ctcacgttaa gggatttttgg tcatgagctt gcgccgtccc gtcaagtcag cgtaatgctc    1080
tgcttaccaa tgcttaatca gtgaggcacc tatctcagcg atctgtctat ttcgttcatc    1140
catagttgcc tgactcccccg tcgtgtagat aactacgata cgggagggct taccatctgg    1200
ccccagcgct gcgatgatac cgcgagaacc acgctcaccg gctccggatt tatcagcaat    1260
aaaccagcca gccggaaggg ccgagcgcag aagtggtcct gcaactttat ccgcctccat    1320
ccagtctatt aattgttgcc gggaagctag agtaagtagt tcgccagtta atagtttgcg    1380
caacgttgtt gccatcgcta caggcatcgt ggtgtcacgc tcgtcgtttg gtatggcttc    1440
attcagctcc ggttcccaac gatcaaggcg agttacatga tcccccatgt tgtgcaaaaa    1500
agcggttagc tccttcggtc ctccgatcgt tgtcagaagt aagttggccg cagtgttatc    1560
actcatggtt atggcagcac tgcataattc tcttactgtc atgccatccg taagatgctt    1620
ttctgtgact ggtgagtact caaccaagtc attctgagaa tagtgtatgc ggcgaccgag    1680
ttgctcttgc ccggcgtcaa tacgggataa taccgcgcca catagcagaa ctttaaaagt    1740
gctcatcatt ggaaaacgtt cttcggggcg aaaactctca aggatcttac cgctgttgag    1800
atccagttcg atgtaaccca ctcgtgcacc caactgatct tcagcatctt ttactttcac    1860
cagcgtttct gggtgagcaa aaacaggaag gcaaaatgcc gcaaaaaagg gaataagggc    1920
gacacggaaa tgttgaatac tcatattctt ccttttttcaa tattattgaa gcatttatca    1980
gggttattgt ctcatgagcg gatacatatt tgaatgtatt tagaaaaata acaaataggg    2040
ggtcagtgtt acaaccaatt aaccaattct gaacattatc gcgagcccat ttatacctga    2100
atatggctca taacacccct tgcagtgcga ctaacggcat gaagctcgtc ggggaaataa    2160
tgattttatt ttgactgata gtgacctgtt cgttgcaaca aattgataag caatgctttc    2220
ttataatgcc aactttgtac aagaaagctg gtccatggaa agctcgacga agcgctaatt    2280
atgaaccaaa tagttgggac tacgattttc tattatcctc tgatacggat gagtccattg    2340
aagtttataa ggataaagct aagaaattgg aagccgaagt gcgccgcgaa attaacaatg    2400
agaaagcgga ttttttgacc ttattagaac tcatcgataa tgtgcaacga ctgggattgg    2460
gctatcggtt tgaaagtgac atccgccggg cactggatcg ttttgtatct agtggcggct    2520
ttgatggcgt cactaaaact agtttgcacg cgaccgcact cagttttcgg ctattacgtc    2580
aacacggttt cgaagtgagt caagaggcgt ttagtggctt caaagatcaa aatggcaatt    2640
ttctggaaaa cttgaaagaa gacacaaaag ctatcctaag tttatacgaa gctagttttc    2700
tcgcgctgga aggtgaaaat attctggatg aggctcgtgt atttgcaatt tctcacctga    2760
aagaattatc tgaagaaaag attggcaaag aactcgccga acaggtaaat cacgccttgg    2820
aactgcccct ccatcgtcgt acccaacgat tggaagctgt gtggagtatc gaagcctatc    2880
gcaagaaaga agacgctaac caagttttgt tggaactggc catcttggat tataacatga    2940
ttcaatccgt atatcagcgc gatctacgtg aaacgtctcg gtggtggcgg cgtgttgggc    3000
tcgctactaa attacatttt gcaaggatc gactcattga atcctttat tgggccgtcg    3060
gggtggcttt tgaaccccag tacagcgatt gccgtaattc tgtagcaaaa atgttttctt    3120
tcgttacaat tatttgatgac atttatgacg tttacggcac cctcgacgaa ctggaattgt    3180
tcactgacgc tgtgtggaacgt tgggacgtaa atgccattaa tgacctgcca gattacatga    3240
agttgtgttt tctcgcgtta tataacacca ttaatgaaat tgcatacgac aatttaaagg    3300
ataagggaga gaatattctg ccttatttga cgaaagcctg gccgatttg tgtaatgcct    3360
ttttgcagga agctaaatgg ttatataaca aatccacccc cacttttgat gactattttg    3420
```

-continued

```
gcaatgcctg aagagcagc agcgggcctc tccaactgat ttttgcttat tttgcggtag    3480
tacaaaacat taagaaagaa gagattgaaa atttgcaaaa gtaccatgac attattagtc    3540
ggcccagtca tattttccgc ttgtgcaacg acctggcatc cgctagtgcc gaaattgcgc    3600
gtggcgaaac agctaatagt gtgagttgtt acatgcgcac aaagggcatt tccgaagaac    3660
tagctacgga aagtgtcatg aacctgattg acgagacttg caagaaaatg aataaggaaa    3720
aattgggcgg gtccctatttt gccaaaccct ttgtggaaac cgcgattaat ttggctcgcc    3780
aaagtcattg tacctatcac aatggtgatg ctcacaccag tcccgatgaa ttaacccgta    3840
aacgagttct gtctgtgatt actgaaccca ttttgcccctt tgaacgttaa aagtaacagg    3900
ttttccatgt tgtcgtctgc aagaacactg cagagcctgc tttttttgtac aaagttggca    3960 ttata                                                                 3965
```

<210> SEQ ID NO 6
<211> LENGTH: 544
<212> TYPE: PRT
<213> ORGANISM: Artificial Sequence
<220> FEATURE:
<223> OTHER INFORMATION: Description of Artificial Sequence:65 kD
  Populus alba isoprene synthase (IspS) gene with chloroplast
  targeting sequence omitted fusion protein from Synechocystis sp.
  cyanobacteria (Ss-IspS) expression plasmid pIspS

<400> SEQUENCE: 6

```
Met Glu Ala Arg Arg Ser Ala Asn Tyr Glu Pro Asn Ser Trp Asp Tyr
  1               5                  10                  15

Asp Phe Leu Leu Ser Ser Asp Thr Asp Glu Ser Ile Glu Val Tyr Lys
             20                  25                  30

Asp Lys Ala Lys Lys Leu Glu Ala Glu Val Arg Arg Glu Ile Asn Asn
         35                  40                  45

Glu Lys Ala Glu Phe Leu Thr Leu Leu Glu Leu Ile Asp Asn Val Gln
     50                  55                  60

Arg Leu Gly Leu Gly Tyr Arg Phe Glu Ser Asp Ile Arg Arg Ala Leu
 65                  70                  75                  80

Asp Arg Phe Val Ser Ser Gly Gly Phe Asp Gly Val Thr Lys Thr Ser
                 85                  90                  95

Leu His Ala Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Thr Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Arg Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
```

245                 250                 255
Lys Asp Arg Leu Ile Glu Ser Phe Tyr Trp Ala Val Gly Val Ala Phe
            260                 265                 270
Glu Pro Gln Tyr Ser Asp Cys Arg Asn Ser Val Ala Lys Met Phe Ser
        275                 280                 285
Phe Val Thr Ile Ile Asp Asp Ile Tyr Asp Val Tyr Gly Thr Leu Asp
    290                 295                 300
Glu Leu Glu Leu Phe Thr Asp Ala Val Glu Arg Trp Asp Val Asn Ala
305                 310                 315                 320
Ile Asn Asp Leu Pro Asp Tyr Met Lys Leu Cys Phe Leu Ala Leu Tyr
                325                 330                 335
Asn Thr Ile Asn Glu Ile Ala Tyr Asp Asn Leu Lys Asp Lys Gly Glu
            340                 345                 350
Asn Ile Leu Pro Tyr Leu Thr Lys Ala Trp Ala Asp Leu Cys Asn Ala
        355                 360                 365
Phe Leu Gln Glu Ala Lys Trp Leu Tyr Asn Lys Ser Thr Pro Thr Phe
    370                 375                 380
Asp Asp Tyr Phe Gly Asn Ala Trp Lys Ser Ser Ser Gly Pro Leu Gln
385                 390                 395                 400
Leu Ile Phe Ala Tyr Phe Ala Val Val Gln Asn Ile Lys Lys Glu Glu
                405                 410                 415
Ile Glu Asn Leu Gln Lys Tyr His Asp Ile Ile Ser Arg Pro Ser His
            420                 425                 430
Ile Phe Arg Leu Cys Asn Asp Leu Ala Ser Ala Ser Ala Glu Ile Ala
        435                 440                 445
Arg Gly Glu Thr Ala Asn Ser Val Ser Cys Tyr Met Arg Thr Lys Gly
    450                 455                 460
Ile Ser Glu Glu Leu Ala Thr Glu Ser Val Met Asn Leu Ile Asp Glu
465                 470                 475                 480
Thr Cys Lys Lys Met Asn Lys Lys Leu Gly Gly Ser Leu Phe Ala
                485                 490                 495
Lys Pro Phe Val Glu Thr Ala Ile Asn Leu Ala Arg Gln Ser His Cys
        500                 505                 510
Thr Tyr His Asn Gly Asp Ala His Thr Ser Pro Asp Glu Leu Thr Arg
    515                 520                 525
Lys Arg Val Leu Ser Val Ile Thr Glu Pro Ile Leu Pro Phe Glu Arg
        530                 535                 540

<210> SEQ ID NO 7
<211> LENGTH: 3133
<212> TYPE: DNA
<213> ORGANISM: Pueraria montana var. lobata
<220> FEATURE:
<223> OTHER INFORMATION: kudzu vine isoprene synthase (IspS) cDNA

<400> SEQUENCE: 7
aatcaatata taatatttac ggaagatttg atgcctttcc tgattttaat ttatttttat    60
ccctgcataa ataattgtg gtcaccgtac actgttcttg tcacttggac aagaaatttg    120
actagcaagc aaggtataat cattcatcta aacttatggt gatttattgc cccacctcat    180
caattttcgt gtgttttatt ttagtgtcct tggatcctcg ttcaatata aaaggagaac    240 atggcatcgc aatttttagag catatcattg aaaagtcatg gcaaccaacc ttttatgctt    300
gtctaataaa ttatcgtccc ccacaccaac accaagtact agatttccac aaagtaagaa    360
cttcatcaca caaaaaacat ctcttgccaa tcccaaacct tggcgagtta tttgtgctac    420

| | | |
|---|---|---|
| gagctctcaa tttacccaaa taacagaaca taatagtcgg cgttcagcta attaccagcc | 480 |
| aaacctctgg aattttgaat ttctgcagtc tctggaaaat gaccttaagg tgattataca | 540 |
| tatattccag ttaattttc tttttttctt ttgtgatttt taaggaatca tttagtttgg | 600 |
| gaaagtattt tttttatttg cacttttaat tataaaaatg ttatatcatt ttcacttttt | 660 |
| tctattcatt ttcaaaattt tacatagaaa acagtaaatt tttattttt tttatttct | 720 |
| attttcatta tttctcaaat caaacggtat taaagcataa acaaagaaat taatattgtt | 780 |
| cttttaattt tatttttta caataatggg aacgattata tattaggctg accttaataa | 840 |
| gttattttt tttataata ttgttcttat tgtaacctaa cgacaggtgg aaaaactaga | 900 |
| agagaaggca acaaagctag aggaggaggt acgatgcatg atcaacagag tagacacaca | 960 |
| accattaagc ttactagaat tgatcgacga tgtccagcgt ctaggattga cctacaagtt | 1020 |
| tgagaaggac ataatcaaag cccttgagaa tattgttttg ctggatgaga ataagaaaaa | 1080 |
| taaaagtgac ctccatgcta ctgctctcag cttccgttta cttagacaac atggctttga | 1140 |
| ggtttcccaa ggtatttatg tatatatatg ttacccactt agcaacatat atatatatat | 1200 |
| atattatgat tcactgacca tgcatgtggt gcagatgtgt ttgagagatt taaggacaag | 1260 |
| gagggaggtt tcagtggtga acttaaaggt gatgtgcaag ggttgctgag tctatatgaa | 1320 |
| gcatcctatc ttggctttga gggagaaaat ctcttggagg aggcaaggac attttcaata | 1380 |
| acacatctca agaacaacct aaaagaagga ataaacacca aagtggcaga acaagttagt | 1440 |
| catgcactgg aacttcccta tcatcaaaga ttgcatagac tagaagcacg atggttcctt | 1500 |
| gacaaatatg aaccaaagga acccaccat cagttactac tcgagcttgc aaagctagat | 1560 |
| ttcaatatgg tgcaaacatt gcaccagaaa gaactgcaag acctgtcaag gttagaaatt | 1620 |
| tcaattctca agtaattatt acctcataag aaattaaata acaataacaa tattgagtgt | 1680 |
| agagatttcc aattaaaaat taacatacga gaggatcaat atatattctt aggtatgtgg | 1740 |
| tactaatgaa atatatgcta ggtggtggac ggagatgggg ctagcaagca agctagactt | 1800 |
| tgtccgagac agattaatgg aagtgtattt ttgggcgttg ggaatggcac ctgatcctca | 1860 |
| attcggtgaa tgtcgtaaag ctgtcactaa aatgtttgga ttggtcacca tcatcgatga | 1920 |
| tgtatatgac gtttatggta ctttggatga gctacaactc ttcactgatg ctgttgagag | 1980 |
| gttcgtaatt gatttcagtc tcgattcagt tggaatttaa ttattgctta attaataata | 2040 |
| acttgcgtac atgcatacac acagatggga cgtgaatgcc ataaacacac ttccagacta | 2100 |
| catgaagttg tgcttcctag cactttataa caccgtcaat gacacgtctt atagcatcct | 2160 |
| taaagaaaaa ggacacaaca accttttccta tttgacaaaa tctgtacata tatactaatt | 2220 |
| atctccttgg ttgattaatt agtttagttt agtttagttg gtatgtcaac acaattaatt | 2280 |
| aatattatat atggatgttg acagtggcgt gagttatgca aagcattcct tcaagaagca | 2340 |
| aaatggtcga acaacaaaat cattccagca tttagcaagt acctggaaaa tgcatcggtg | 2400 |
| tcctcctccg gtgtggcttt gcttgctcct tcctacttct cagtgtgcca acaacaagaa | 2460 |
| gatatctcag accatgctct tcgttctttta actgatttcc atggccttgt gcgctcctca | 2520 |
| tgcgtcattt tcagactctg caatgatttg gctacctcag cggtgtgtaa ttaattacct | 2580 |
| taattaattt gtaacacttg ttagactaat atatataggt gtgtctgtta attactacag | 2640 |
| gctgagctag agagggtga gacgacaaat tcaataatat cttatatgca tgagaatgac | 2700 |
| ggcacttctg aagagcaagc acgtgaggag ttgagaaaat tgatcgatgc agagtggaag | 2760 |
| aagatgaacc gagagcgagt ttcagattct acactactcc caaaagcttt tatggaaata | 2820 |

-continued

```
gctgttaaca tggctcgagt ttcgcattgc acataccaat atggagacgg acttggaagg   2880
ccagactacg ccacagagaa tagaatcaag ttgctactta tagacccctt tccaatcaat   2940
caactaatgt acgtgtaaca acacaatata aacactttt c tacaagtata tatttgttta   3000
atttcggtgt tgaattaggg gtcaacacag ctatatatac ttcaatggac caactcaacc   3060
aatctgataa gagaaaaaaa ataaaaataa ggttaggtta actttgtata aatccaagtt   3120
agatatcaag ttt                                                      3133
```

<210> SEQ ID NO 8
<211> LENGTH: 608
<212> TYPE: PRT
<213> ORGANISM: Pueraria montana var. lobata
<220> FEATURE:
<223> OTHER INFORMATION: kudzu vine isoprene synthase (IspS)

<400> SEQUENCE: 8

```
Met Ala Thr Asn Leu Leu Cys Leu Ser Asn Lys Leu Ser Ser Pro Thr
  1               5                  10                  15

Pro Thr Pro Ser Thr Arg Phe Pro Gln Ser Lys Asn Phe Ile Thr Gln
                 20                  25                  30

Lys Thr Ser Leu Ala Asn Pro Lys Pro Trp Arg Val Ile Cys Ala Thr
             35                  40                  45

Ser Ser Gln Phe Thr Gln Ile Thr Glu His Asn Ser Arg Arg Ser Ala
         50                  55                  60

Asn Tyr Gln Pro Asn Leu Trp Asn Phe Glu Phe Leu Gln Ser Leu Glu
 65                  70                  75                  80

Asn Asp Leu Lys Val Glu Lys Leu Glu Glu Lys Ala Thr Lys Leu Glu
                 85                  90                  95

Glu Glu Val Arg Cys Met Ile Asn Arg Val Asp Thr Gln Pro Leu Ser
            100                 105                 110

Leu Leu Glu Leu Ile Asp Asp Val Gln Arg Leu Gly Leu Thr Tyr Lys
        115                 120                 125

Phe Glu Lys Asp Ile Ile Lys Ala Leu Glu Asn Ile Val Leu Leu Asp
    130                 135                 140

Glu Asn Lys Lys Asn Lys Ser Asp Leu His Ala Thr Ala Leu Ser Phe
145                 150                 155                 160

Arg Leu Leu Arg Gln His Gly Phe Glu Val Ser Gln Asp Val Phe Glu
                165                 170                 175

Arg Phe Lys Asp Lys Glu Gly Gly Phe Ser Gly Glu Leu Lys Gly Asp
            180                 185                 190

Val Gln Gly Leu Leu Ser Leu Tyr Glu Ala Ser Tyr Leu Gly Phe Glu
        195                 200                 205

Gly Glu Asn Leu Leu Glu Glu Ala Arg Thr Phe Ser Ile Thr His Leu
    210                 215                 220

Lys Asn Asn Leu Lys Glu Gly Ile Asn Thr Lys Val Ala Glu Gln Val
225                 230                 235                 240

Ser His Ala Leu Glu Leu Pro Tyr His Gln Arg Leu His Arg Leu Glu
                245                 250                 255

Ala Arg Trp Phe Leu Asp Lys Tyr Glu Pro Lys Glu Pro His His Gln
            260                 265                 270

Leu Leu Leu Glu Leu Ala Lys Leu Asp Phe Asn Met Val Gln Thr Leu
        275                 280                 285

His Gln Lys Glu Leu Gln Asp Leu Ser Arg Trp Trp Thr Glu Met Gly
    290                 295                 300

Leu Ala Ser Lys Leu Asp Phe Val Arg Asp Arg Leu Met Glu Val Tyr
```

```
                    305                 310                 315                 320

Phe Trp Ala Leu Gly Met Ala Pro Asp Pro Gln Phe Gly Glu Cys Arg
                            325                 330                 335

Lys Ala Val Thr Lys Met Phe Gly Leu Val Thr Ile Ile Asp Asp Val
                            340                 345                 350

Tyr Asp Val Tyr Gly Thr Leu Asp Glu Leu Gln Leu Phe Thr Asp Ala
                            355                 360                 365

Val Glu Arg Trp Asp Val Asn Ala Ile Asn Thr Leu Pro Asp Tyr Met
                        370                 375                 380

Lys Leu Cys Phe Leu Ala Leu Tyr Asn Thr Val Asn Asp Thr Ser Tyr
            385                 390                 395                 400

Ser Ile Leu Lys Glu Lys Gly His Asn Asn Leu Ser Tyr Leu Thr Lys
                            405                 410                 415

Ser Trp Arg Glu Leu Cys Lys Ala Phe Leu Gln Glu Ala Lys Trp Ser
                            420                 425                 430

Asn Asn Lys Ile Ile Pro Ala Phe Ser Lys Tyr Leu Glu Asn Ala Ser
                            435                 440                 445

Val Ser Ser Gly Val Ala Leu Leu Ala Pro Ser Tyr Phe Ser Val
                450                 455                 460

Cys Gln Gln Gln Glu Asp Ile Ser Asp His Ala Leu Arg Ser Leu Thr
            465                 470                 475                 480

Asp Phe His Gly Leu Val Arg Ser Ser Cys Val Ile Phe Arg Leu Cys
                            485                 490                 495

Asn Asp Leu Ala Thr Ser Ala Ala Glu Leu Glu Arg Gly Glu Thr Thr
                            500                 505                 510

Asn Ser Ile Ile Ser Tyr Met His Glu Asn Asp Gly Thr Ser Glu Glu
                            515                 520                 525

Gln Ala Arg Glu Glu Leu Arg Lys Leu Ile Asp Ala Glu Trp Lys Lys
                        530                 535                 540

Met Asn Arg Glu Arg Val Ser Asp Ser Thr Leu Leu Pro Lys Ala Phe
            545                 550                 555                 560

Met Glu Ile Ala Val Asn Met Ala Arg Val Ser His Cys Thr Tyr Gln
                            565                 570                 575

Tyr Gly Asp Gly Leu Gly Arg Pro Asp Tyr Ala Thr Glu Asn Arg Ile
                            580                 585                 590

Lys Leu Leu Leu Ile Asp Pro Phe Pro Ile Asn Gln Leu Met Tyr Val
                        595                 600                 605

<210> SEQ ID NO 9
<211> LENGTH: 595
<212> TYPE: PRT
<213> ORGANISM: Populus tremuloides
<220> FEATURE:
<223> OTHER INFORMATION: quaking aspen isoprene synthase (IspS)

<400> SEQUENCE: 9

Met Ala Thr Glu Leu Leu Cys Leu His Arg Pro Ile Ser Leu Thr His
 1               5                  10                  15

Lys Leu Phe Arg Asn Pro Leu Pro Lys Val Ile Gln Ala Thr Pro Leu
                20                  25                  30

Thr Leu Lys Leu Arg Cys Ser Val Ser Thr Glu Asn Val Ser Phe Ser
            35                  40                  45

Glu Thr Glu Thr Glu Thr Arg Arg Ser Ala Asn Tyr Glu Pro Asn Ser
        50                  55                  60

Trp Asp Tyr Asp Tyr Leu Leu Ser Ser Asp Thr Asp Glu Ser Ile Glu
65                  70                  75                  80
```

```
Val His Lys Asp Lys Ala Lys Lys Leu Glu Ala Glu Val Arg Arg Glu
            85                  90                  95
Ile Asn Asn Glu Lys Ala Glu Phe Leu Thr Leu Leu Glu Leu Ile Asp
            100                 105                 110
Asn Val Gln Arg Leu Gly Leu Gly Tyr Arg Phe Glu Ser Asp Ile Arg
            115                 120                 125
Arg Ala Leu Asp Arg Phe Val Ser Ser Gly Gly Phe Asp Gly Val Thr
130                 135                 140
Lys Thr Ser Leu His Gly Thr Ala Leu Ser Phe Arg Leu Leu Arg Gln
145                 150                 155                 160
His Gly Phe Glu Val Ser Gln Glu Ala Phe Ser Gly Phe Lys Asp Gln
            165                 170                 175
Asn Gly Asn Phe Leu Glu Asn Leu Lys Glu Asp Ile Lys Ala Ile Leu
            180                 185                 190
Ser Leu Tyr Glu Ala Ser Phe Leu Ala Leu Glu Gly Glu Asn Ile Leu
            195                 200                 205
Asp Glu Ala Lys Val Phe Ala Ile Ser His Leu Lys Glu Leu Ser Glu
210                 215                 220
Glu Lys Ile Gly Lys Glu Leu Ala Glu Gln Val Ser His Ala Leu Glu
225                 230                 235                 240
Leu Pro Leu His Arg Arg Thr Gln Arg Leu Glu Ala Val Trp Ser Ile
            245                 250                 255
Glu Ala Tyr Arg Lys Lys Glu Asp Ala Asn Gln Val Leu Leu Glu Leu
            260                 265                 270
Ala Ile Leu Asp Tyr Asn Met Ile Gln Ser Val Tyr Gln Arg Asp Leu
            275                 280                 285
Arg Glu Thr Ser Arg Trp Trp Arg Arg Val Gly Leu Ala Thr Lys Leu
290                 295                 300
His Phe Ala Arg Asp Arg Leu Ile Glu Ser Phe Tyr Trp Ala Val Gly
305                 310                 315                 320
Val Ala Phe Glu Pro Gln Tyr Ser Asp Cys Arg Asn Ser Val Ala Lys
            325                 330                 335
Met Phe Ser Phe Val Thr Ile Ile Asp Asp Ile Tyr Asp Val Tyr Gly
            340                 345                 350
Thr Leu Asp Glu Leu Glu Leu Phe Thr Asp Ala Val Glu Arg Trp Asp
            355                 360                 365
Val Asn Ala Ile Asn Asp Leu Pro Asp Tyr Met Lys Leu Cys Phe Leu
370                 375                 380
Ala Leu Tyr Asn Thr Ile Asn Glu Ile Ala Tyr Asp Asn Leu Lys Asp
385                 390                 395                 400
Lys Gly Glu Asn Ile Leu Pro Tyr Leu Thr Lys Ala Trp Ala Asp Leu
            405                 410                 415
Cys Asn Ala Phe Leu Gln Glu Ala Lys Trp Leu Tyr Asn Lys Ser Thr
            420                 425                 430
Pro Thr Phe Asp Asp Tyr Phe Gly Asn Ala Trp Lys Ser Ser Ser Gly
            435                 440                 445
Pro Leu Gln Leu Ile Phe Ala Tyr Phe Ala Val Val Gln Asn Ile Lys
            450                 455                 460
Lys Glu Glu Ile Glu Asn Leu Gln Lys Tyr His Asp Ile Ile Ser Arg
465                 470                 475                 480
Pro Ser His Ile Phe Arg Leu Cys Asn Asp Leu Ala Ser Ala Ser Ala
            485                 490                 495
Glu Ile Ala Arg Gly Glu Thr Ala Asn Ser Val Ser Cys Tyr Met Arg
```

```
                    500                 505                 510
Thr Lys Gly Ile Ser Glu Glu Leu Ala Thr Glu Ser Val Met Asn Leu
        515                 520                 525

Ile Asp Glu Thr Trp Lys Lys Met Asn Lys Glu Lys Leu Gly Gly Ser
    530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
        595

<210> SEQ ID NO 10
<211> LENGTH: 595
<212> TYPE: PRT
<213> ORGANISM: Populus nigra
<220> FEATURE:
<223> OTHER INFORMATION: Lombardy poplar isoprene synthase (IspS)

<400> SEQUENCE: 10

Met Ala Thr Glu Leu Leu Cys Leu His Arg Pro Ile Ser Leu Thr His
  1               5                  10                  15

Lys Leu Phe Arg Asn Pro Leu Pro Lys Val Ile Gln Ala Thr Pro Leu
             20                  25                  30

Thr Leu Lys Leu Arg Cys Ser Val Ser Thr Glu Asn Val Ser Phe Thr
         35                  40                  45

Glu Thr Glu Thr Glu Thr Arg Arg Ser Ala Asn Tyr Glu Pro Asn Ser
     50                  55                  60

Trp Asp Tyr Asp Tyr Leu Leu Ser Ser Asp Thr Asp Glu Ser Ile Glu
 65                  70                  75                  80

Val Tyr Lys Asp Lys Ala Lys Lys Leu Glu Ala Glu Val Arg Arg Glu
                 85                  90                  95

Ile Asn Asn Glu Lys Ala Glu Phe Leu Thr Leu Pro Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Ala Val Thr
    130                 135                 140

Lys Thr Ser Leu His Ala Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Lys Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Lys Val Phe Ala Ile Ser His Leu Lys Glu Leu Ser Glu
    210                 215                 220

Glu Lys Ile Gly Lys Asp Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asp Gln Val Leu Leu Glu Leu
            260                 265                 270
```

-continued

```
Ala Ile Leu Asp Tyr Asn Met Ile Gln Ser Val Tyr Gln Arg Asp Leu
            275                 280                 285

Arg Glu Thr Ser Arg Trp Trp Arg Arg Val Gly Leu Ala Thr Lys Leu
        290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asp Asp Leu Pro Asp Tyr Met Lys Leu Cys Phe Leu
370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
            420                 425                 430

Pro Thr Phe Asp Glu Tyr Phe Gly Asn Ala Trp Lys Ser Ser Ser Gly
        435                 440                 445

Pro Leu Gln Leu Val Phe Ala Tyr Phe Ala Val Val Gln Asn Ile Lys
450                 455                 460

Lys Glu Glu Ile Asp Asn Leu Gln Lys Tyr His Asp Ile Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
            500                 505                 510

Thr Lys Gly Ile Ser Glu Glu Leu Ala Thr Glu Ser Val Met Asn Leu
        515                 520                 525

Ile Asp Glu Thr Trp Lys Lys Met Asn Lys Glu Lys Leu Gly Gly Ser
530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
        595

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:beginning
      sequence of white poplar isoprene synthase (IspS)
      mature protein with chloroplast transit peptide
      omitted

<400> SEQUENCE: 11

Cys Ser Val Ser Thr Glu Asn
 1               5
```

```
<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer IspS_F_NdeI

<400> SEQUENCE: 12
ctgggtcata tggaagctcg acgaa                                              25

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:PCR
      amplification primer IspS_R_HindIII

<400> SEQUENCE: 13
atggaaaacc tgaagctttt aacgttcaa                                          29
```

US 7,947,478 B2

SHORT CHAIN VOLATILE HYDROCARBON PRODUCTION USING GENETICALLY ENGINEERED MICROALGAE, CYANOBACTERIA OR BACTERIA

CROSS-REFERENCE TO RELATED APPLICATIONS

This application claims benefit of U.S. provisional application No. 60/806,244, filed Jun. 29, 2006, which application is herein incorporated by reference.

BACKGROUND OF THE INVENTION

A variety of herbaceous, deciduous and conifer plants are known to possess the genetic and enzymatic capability for the synthesis and release of short-chain isoprenoids (e.g., isoprene ($C_5H_8$) and methyl-butenol ($C_5H_{10}O_1$)) into the surrounding environment. Such short-chain isoprenoids are derived from the early Calvin-cycle products of photosynthesis, and can be synthesized in the chloroplast of herbaceous, deciduous and conifer plants via the so-called DXP-MEP pathway at substantial rates under certain environmental stress conditions. Heat-stress of the organism is particularly important for the induction of this process in plants, and the resulting hydrocarbon pollution of the atmosphere has been the focus of the prior art in this field.

Emission of isoprene from herbaceous, deciduous, and conifer plants is due to the presence of an isoprene synthase (IspS) gene, a nuclear gene encoding for a chloroplast-localized protein that catalyzes the conversion of dimethylallyl diphosphate (DMAPP) to isoprene. As noted above, isoprenoids are synthesized in the chloroplast from the early products of the Calvin cycle (carbon fixation and reduction, see FIG. 1). 5-carbon isoprenoids, e.g. isoprene ($C_5H_8$) and methyl-butenol ($C_5H_{10}O_1$) are relatively small hydrophobic molecules, synthesized directly from DMAPP (FIG. 2). These isoprenoids are volatile molecules that easily go through cellular membranes and thereby are emitted from the leaves into the atmosphere. The process of heat stress-induction and emission of short-chain hydrocarbons by plants has been discussed as undesirable pollution of the atmosphere in the literature. There has been no description of the mass-generation, harvesting and sequestration of these hydrocarbons from the leaves of herbaceous, deciduous and conifer plants.

There is an urgent need for the development of renewable biofuels that will help meet global demands for energy but without contributing to climate change. The current invention addresses this need by providing methods and compositions to generate volatile short-chain hydrocarbons that are derived entirely from sunlight, carbon dioxide ($CO_2$) and water ($H_2O$). These hydrocarbons can serve as biofuel or feedstock in the synthetic chemistry industry.

BRIEF SUMMARY OF THE INVENTION

The invention is based, in part, on the discovery that microalgae, cyanobacteria and prokaryotic photosynthesis can be employed, upon suitable modification, to produce 5-carbon isoprenoids (e.g. FIG. 3). The DXP-MEP isoprenoid biosynthetic pathway is absolutely required in plants and algae, as it leads to the synthesis of many essential longer-chain cellular compounds. Unicellular green algae specifically express this pathway in their chloroplast and utilize the corresponding enzymes for the biosynthesis of a great variety of molecules (carotenoids, tocopherols, phytol, sterols, hormones, among many others). The present invention relates to methods and compositions for the use of genetically modified microalgae, cyanobacteria, and photosynthetic and non-photosynthetic bacteria in the production and harvesting of 5-carbon volatile isoprenoid compounds, e.g., isoprene and methyl-butenol. Such genetically modified organisms can be used commercially in an enclosed mass culture system, e.g., to provide a source of renewable fuel for internal combustion engines or, upon on-board reformation, in fuel-cell operated engines; or to provide a source of isoprene for uses in other chemical processes such as chemical synthesis.

Microalgae, cyanobacteria, and photosynthetic and non-photosynthetic bacteria do not possess an isoprene synthase or a methyl-butenol synthase gene, which catalyze the last committed step in isoprene ($C_5H_8$) and methyl-butenol ($C_5H_{10}O_1$) biosynthesis, respectively. This invention therefore provides methods and compositions to genetically modify microorganisms to express an isoprene synthase gene, e.g., a codon-adjusted poplar isoprene synthase gene, so as to confer isoprene ($C_5H_8$) production to the organism.

In additional aspects, the invention also provides method and compositions for the genetic modification of microalgae, cyanobacteria, and photosynthetic and non-photosynthetic bacteria to confer to these micro-organisms over-expression of endogenous genes and proteins encoding the first committed step in isoprenoid biosynthesis. The invention can thus further comprise increasing expression of native Dxs and Dxr genes in the microorganism, e.g., green algae such as *Chlamydomonas reinhardtii*; cyanobacteria such as *Synechocystis* sp.; or photosynthetic bacteria such as *Rhodospirillum rubrum*, or non-photosynthetic bacteria such as *Escherichia coli*. Dxs and Dxr encode enzymes that catalyze the first committed steps in isoprenoid biosynthesis.

In some embodiments, microalgae are employed. Microalgae are factories of photosynthesis, with the chloroplast occupying ~70% of the cell volume; green algal chloroplast contains over 3 million electron transport circuits, each being capable of delivering 100 electrons per second to the Calvin Cycle for $CO_2$ conversion to GA-3-P; microalgae have no roots, stems, leaves, or flowers on which to invest photosynthetic resources, thus a greater fraction of photosynthetic product can be directed toward volatile isoprenoid generation; microalgae grow and reproduce faster than any other terrestrial or aquatic plant, doubling of biomass per day; and microalgae are non-toxic and non-polluting, thus environmentally friendly for mass cultivation and commercial exploitation. Accordingly, in some embodiments, the invention provides a process to modify the highly efficient process of microalgal photosynthesis to generate, in high volume, short-chain isoprene hydrocarbons (e.g., $C_5H_8$) from sunlight, $CO_2$ and $H_2O$. Such modified microalgae can be grown, e.g., in large capacity (e.g., 1,000-1,000,000 liters) fully enclosed photoreactors for the production and harvesting of volatile short-chain isoprene hydrocarbons.

The invention will help eliminate a number of current barriers in the commercial production, storage and utilization of renewable energy, including, but not limited to: (a) Lowering the cost of production and storage of fuel. (b) Improving fuel Weight/Volume ratios. (c) Improving the efficiency of fuel production/storage. (d) Increasing the durability of fuel storage. (e) Minimizing auto-refueling time. (f) Offering sufficient fuel storage for acceptable vehicle range. (g) Producing a fuel amenable to regeneration process. (h) Fuel is not subject to interference by oxygen in either production or storage stage.

In one aspect, the invention provides a method of producing isoprene hydrocarbons in a microorganism selected from the group consisting of microalgae, cyanobacteria, or photosynthetic bacteria, the method comprising: introducing an expression cassette that comprises a nucleic acid sequence encoding isoprene synthase into the microorganism; and culturing the microorganism under conditions in which the nucleic acid encoding isoprene synthase is expressed. In some embodiments, the microorganism is a microalgae such as green algae, e.g., *Chlamydomonas reinhardtii, Scenedesmus obliquus, Chlorella vulgaris* or *Dunaliella salina*. In alternative embodiments, the microorganism is a cyanobacteria, such as a *Synechocystis* sp. In other embodiments the microorganism is a photosynthetic bacteria such as *Rhodospirillum rubrum*. Alternatively, in some embodiments, the microorganism can be a non-photosynthetic bacteria, such as *Escherichia coli*.

In some embodiments, the nucleic acid introduced into the microorganism comprises a sequence that encodes an isoprene synthase polypeptide that has the sequence set forth in SEQ ID NO:2, or has the sequence set forth in SEQ ID NO:2, but lacks a transit peptide region. The isoprene synthase polypeptide can, e.g., comprise amino acid residues 53-595 of SEQ ID NO:2, or residues 38-595 of SEQ ID NO:2. In some embodiment, the nucleic acid comprises the sequence set forth in SEQ ID NO:1. In other embodiments, the nucleic acid comprises the nucleotide coding sequence for isoprene synthase set forth in SEQ ID NO:3; or the nucleic acid comprises the isoprene coding sequence as set forth in SEQ ID NO:5.

In another aspect, the invention provides a microorganism selected from the group consisting of a microalgae cell, a cyanobacteria cell, and a photosynthetic bacterial cell or non-photosynthetic bacterial cell, wherein the microorganism comprises a heterologous nucleic acid that encodes isoprene synthase and is operably linked to a promoter. The promoter can be a constitutive promoter or an inducible promoter. In some embodiments, the microorganism is a green algae, such as *Chlamydomonas reinhardtii, Scenedesmus obliquus, Chlorella vulgaris* or *Dunaliella salina*. In other embodiments, the microorganism is a cyanobacteria, such as *Synechocystis* sp. In other embodiments, the microorganism is a photosynthetic bacteria, such as *Rhodospirillum rubrum*. In some embodiments, the heterologous nucleic acid comprises a sequence that encodes an isoprene synthase gene that has the sequence set forth in SEQ ID NO:2, or has the sequence set forth in SEQ ID NO:2, but lacks the transit peptide. The isoprene synthase polypeptide can, e.g., comprise amino acid residues 53-595 of SEQ ID NO:2, or residues 38-595 of SEQ ID NO:2. In some embodiments, the nucleic acid comprises the sequence set forth in SEQ ID NO:1. In other embodiments, the nucleic acid comprises the nucleotide coding sequence for isoprene synthase set forth in SEQ ID NO:3; or the nucleic acid comprises the isoprene coding sequence as set forth in SEQ ID NO:5.

In a further aspect, the invention provides a method of producing isoprene hydrocarbons in a microorganism that comprises a heterologous gene that encodes isoprene synthase and that is selected from the group consisting of microalgae, cyanobacteria, photosynthetic bacteria, and non-photosynthetic bacteria, the method comprising: mass-culturing the microorganism in an enclosed bioreactor under conditions in which the isoprene synthase gene is expressed; and harvesting isoprene hydrocarbons produced by the microorganism. In some embodiments, the microorganism is a microalgae that is a green microalgae, such as *Chlamydomonas reinhardtii, Scenedesmus obliquus, Chlorella vulgaris* or *Dunaliella salina*. Alternatively, the microorganism can be a cyanobacteria, such as a *Synechocystis* sp. In other embodiments, the microorganism is a photosynthetic bacteria, such as *Rhodospirillum rubrum*. In still other embodiments, the microorganism is a non-photosynthetic bacteria, such as *Escherichia coli*.

In some embodiments of the mass-culture methods of the invention, the heterologous gene that encodes isoprene synthase comprises a sequence that encodes an isoprene synthase gene that has the sequence set forth in SEQ ID NO:2 or has the sequence set forth in SEQ ID NO:2, but lacks the transit peptide. The isoprene synthase polypeptide can, e.g., comprise amino acid residues 53-595 of SEQ ID NO:2 or residues 38-595 of SEQ ID NO:2. The nucleic acid can, e.g., comprise the sequence set forth in SEQ ID NO:1. In other embodiments, the nucleic acid comprises the nucleotide coding sequence for isoprene synthase set forth in SEQ ID NO:3; or the isoprene coding sequence as set forth in SEQ ID NO:5.

In some embodiments of the methods and compositions of the invention, the IspS nucleic acid encodes a protein that comprises the amino acid sequence of SEQ ID NO:8 or that comprises amino acid 46-608 of SEQ ID NO:8.

BRIEF DESCRIPTION OF THE DRAWINGS

FIG. 13. Clustal alignment of four known isoprene synthase proteins(SEQ ID NOS:2, 9, 10 and 8, respectively).

DETAILED DESCRIPTION OF THE INVENTION

Definitions

Figure 1:
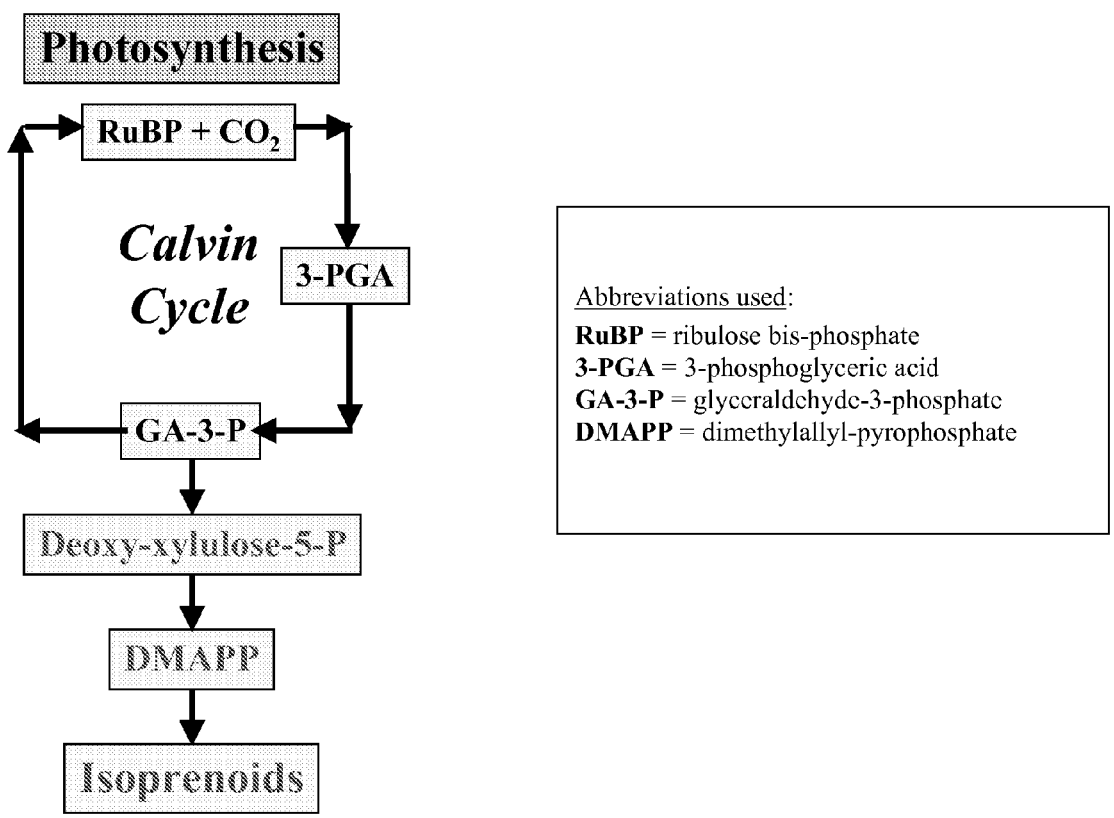
FIG. 1. Schematic pathway of carbon dioxide fixation and reduction in the Calvin cycle of photosynthesis and of the channeling of organic carbon from the ubiquitous glyceraldehyde-3-phosphate (GA-3-P) via the deoxy-xylulose/methyl-erythritol (DXP/MEP) biosynthetic pathway to isoprenoids.
Figure 2:
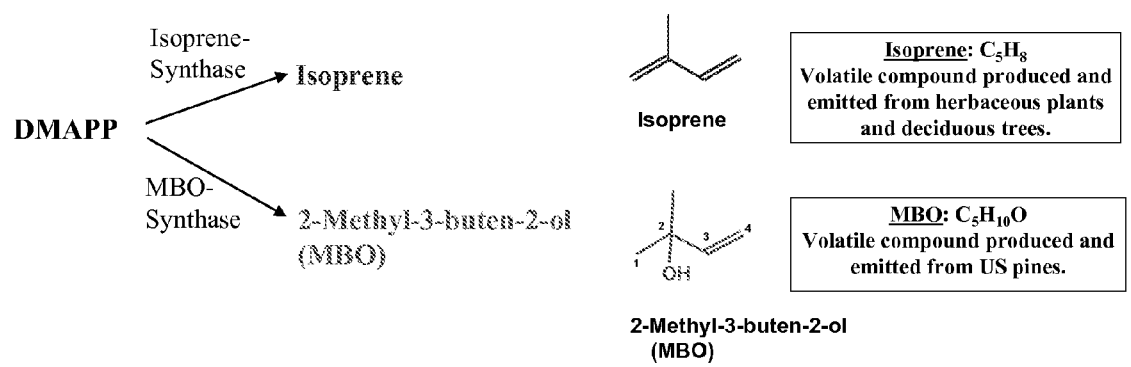
FIG. 2. (Left panel) Single step enzymatic reaction for the biosynthesis of isoprene and methyl-butenol in the chloroplast of herbaceous/deciduous tress and US pines, respectively. (Right panel) Chemical formulae of isoprene ($C_5H_8$) and methyl-butenol ($C_5H_{10}O_1$).
Figure 3:
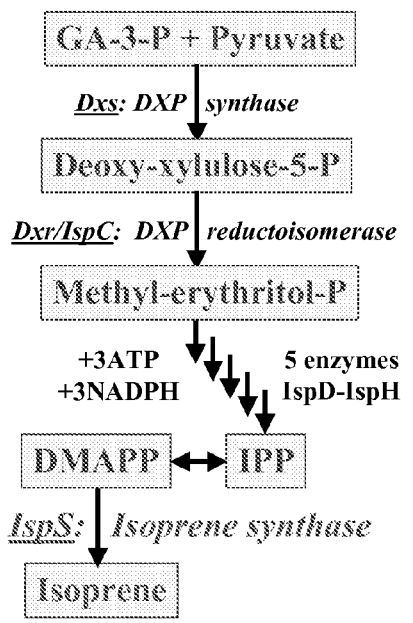
FIG. 3. The DXP/MEP biosynthetic pathway leading to the formation of volatile isoprenoids from the abundant chloroplast metabolites GA-3-P (glyceraldehyde-3-phosphate) and pyruvate. Seven distinct enzymatic reactions are needed to synthesize isoprene from GA-3-P and pyruvate. Unicellular green algae, cyanobacteria, photosynthetic and certain non-photosynthetic bacteria possess the first six of these genes, but lack the isoprene synthase or methyl-butenol synthase genes.

"Microalgae", "alga" or the like, refer to plants belonging to the subphylum Algae of the phylum Thallophyta. The algae are unicellular, photosynthetic, oxygenic algae and are non-parasitic plants without roots, stems or leaves; they contain chlorophyll and have a great variety in size, from microscopic to large seaweeds. Green algae, belonging to Eukaryota—Viridiplantae—Chlorophyta—Chlorophyceae, can be used in the invention. However, algae useful in the invention may also be blue-green, red, or brown, so long as the algae is able to perform the steps necessary to provide a substrate to produce isoprene.

A "volatile isoprene hydrocarbon" in the context of this invention refers to a 5-carbon, short chain isoprenoid, e.g., isoprene or methyl-butenol.

The terms "nucleic acid" and "polynucleotide" are used synonymously and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones. Thus, nucleic acids or polynucleotides may also include modified nucleotides, that permit correct read through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences that may be introduced to conform with codon preference in a specific host cell. In the context of this invention, the term "IspS coding region" when used with reference to a nucleic acid reference sequence such as SEQ ID NO:3, 5, or 7 refers to the region of the nucleic acid that encodes the protein.

An IspS "gene" in the context of this invention refers to a nucleic acid that encodes an IspS protein, or fragment thereof. Thus, such a gene is often a cDNA sequence that encodes IspS. In other embodiments, an IspS gene may include sequences, such as introns that are not present in a cDNA.

The term "promoter" or "regulatory element" refers to a region or sequence determinants located upstream or downstream from the start of transcription that direct transcription. As used herein, a promoter includes necessary nucleic acid sequences near the start site of transcription, such as, in the case of a polymerase II type promoter, a TATA element. A promoter also optionally includes distal elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter) and a second nucleic acid sequence, such as an IspS gene, wherein the expression control sequence directs transcription of the nucleic acid corresponding to the second sequence. An "algae promoter" or "bacterial promoter" is a promoter capable of initiating transcription in algae and/or bacterial cells, respectively. Such a promoter is therefore active in a microalgae, cyanobacteria, or bacteria cell, but need not originate from that organism. It is understood that limited modifications can be made without destroying the biological function of a regulatory element and that such limited modifications can result in algal regulatory elements that have substantially equivalent or enhanced function as compared to a wild type algal regulatory element. These modifications can be deliberate, as through site-directed mutagenesis, or can be accidental such as through mutation in hosts harboring the regulatory element. All such modified nucleotide sequences are included in the definition of an algal regulatory element as long as the ability to confer expression in unicellular green algae is substantially retained.

"Increased" or "enhanced" activity or expression of a Dxs or Dxr gene refers to a change in Dxs or Dxr activity. Examples of such increased activity or expression include the following. Dxs or DxR activity or expression of a Dxs or DxR gene is increased above the level of that in wild-type, non-transgenic control microorganism (i.e., the quantity of Dxs or Dxr activity or expression of Dxs or Dx gene is increased). Dxs or Dxr activity or expression of a Dxs or Dxr gene is in a cell where it is not normally detected in wild-type, non-transgenic cells (i.e., expression of the Dxs or Dxr gene is increased). Dxs or Dxr activity or expression is also increased when Dxs or Dxr activity or expression of the Dxs or Dxr gene is present in a cell for a longer period than in a wild-type, non-transgenic controls (i.e., duration of Dxs or Dxr activity or expression of the Dxs or Dxr gene is increased).

"Expression" of an IspS gene in the context of this invention typically refers introducing an IspS gene into a cell, e.g., microalgae, such as green microalgae, cyanobacteria, or photosynthetic or non-photosynthetic bacteria, in which it is not normally expressed. Accordingly, an "increase" in IspS activity or expression is generally determined relative to wild type cells, e.g., microalgae, cyanobacteria or photosynthetic or non-photosynthetic bacteria, that have no IspS activity.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants An "IspS polynucleotide" is a nucleic acid sequence of SEQ ID NO:1 or SEQ ID NO:7, or the IspS coding regions of SEQ ID NO:3 or SEQ ID NO:5; or a nucleic acid sequence that is substantially similar to SEQ ID NO:1 or the IspS coding regions of SEQ ID NO:3 or SEQ ID NO:5; or a nucleic acid sequence that encodes a polypeptide of SEQ ID NO:2 or SEQ ID NO:8, or a polypeptide that is substantially similar to SEQ ID NO:2 or SEQ ID NO:8, or a fragment or domain thereof. Thus, an IspS polynucleotide: 1) comprises a region of about 15 to about 50, 100, 150, 200, 300, 500, 1,000, 1500, or 2,000 or more nucleotides, sometimes from about 20, or about 50, to about 1800 nucleotides and sometimes from about 200 to about 600 or about 1500 nucleotides of SEQ ID NO:1 or SEQ ID NO:7, or the IspS coding region of SEQ ID NOs: 3 or 5; or 2) hybridizes to SEQ ID NO:1 or SEQ ID NO:7 or to the IspS coding region of SEQ ID NO:3 or SEQ ID NO:5, or the complements thereof, under stringent conditions, or 3) encodes an IspS polypeptide or fragment of at least 50 contiguous amino acids, typically of at least 100, 150, 200, 250, 300, 350, 400, 450, 500, or 550, or more contiguous residues of an IspS polypeptide, e.g., SEQ ID NO:2 or SEQ ID NO:8; or 4) encodes an IspS polypeptide or fragment that has at least 55%, often at least 60%, 65%, 70%, 75%, 80%, 85%, 90%, 95%, or greater identity to SEQ ID NO:2 or SEQ ID NO:8, or over a comparison window of at least 100, 200, 300, 400, 500, or 550 amino acid residues of SEQ ID NO:2 or SEQ ID NO:8; or 5) has a nucleic acid sequence that has greater than about 60%, 65%, 70%, 75%, 80%, 85%, 90%, 95%, 96%, 97%, 98%, 99%, or higher nucleotide sequence identity to SEQ ID NO:1 or SEQ ID NO:7, at least 80%, 85%, 90%, or at least 95%, 96%, 97%, 98%, 99% or greater identity over a comparison window of at least about 50, 100, 200, 500, 1000, or more nucleotides of SEQ ID NO:1 or SEQ ID NO:7, or the IspS coding region of SEQ ID NO:3 or SEQ ID NO:5; or 6) is amplified by primers to SEQ ID NO:1 or SEQ ID NO:7, or the IspS coding region of SEQ ID NO:3 or SEQ ID NO:5. The term "IspS polynucleotide" refers to double stranded or singled stranded nucleic acids. The IspS nucleic acids for use in the invention encode an active IspS that catalyzes the conversion of a dimethylallyl diphosphate substrate to isoprene.

An "IspS polypeptide" is an amino acid sequence that has the amino acid sequence of SEQ ID NO:2 or SEQ ID NO:8, or is substantially similar to SEQ ID NO:2 or SEQ ID NO:8, or a fragment or domain thereof. Thus, an IspS polypeptide can: 1) have at least 55% identity, typically at least 60%, 65%, 70%, 75%, 80%, 85%, 90%, 95% or greater identity to SEQ ID NO:2 or SEQ ID NO:8, or over a comparison window of at least 100, 200, 250, 300, 250, 400, 450, 500, or 550 amino acids of SEQ ID NO:2 or 8; or 2) comprise at least 100, typically at least 200, 250, 300, 350, 400, 450, 500, 550, or more contiguous amino acids of SEQ ID NO:2 or 8; or 3) bind to antibodies raised against an immunogen comprising an amino acid sequence of SEQ ID NO:2 or 8 and conservatively modified variants thereof. An IspS polypeptide in the context of this invention is a functional protein that catalyzes the conversion of a dimethylallyl diphosphate substrate to isoprene.

As used herein, a homolog or ortholog of a particular IspS gene (e.g., SEQ ID NO:1) is a second gene in the same plant type or in a different plant type that is substantially identical (determined as described below) to a sequence in the first gene.

The terms "Dxs" and "Dxr" nucleic acids and polypeptide refer to fragments, variants, and the like. Exemplary Dxs and Dxr sequences include the nucleic acid and polypeptide Dxs and Dxr sequences disclosed in U.S. Patent Application Publication No. 20030219798, e.g., *Chlamydomonas* sequences. The Dxs and Dxr sequences of U.S. Patent Application Publication No. 20030219798 are herein incorporated by reference.

An "expression cassette" refers to a nucleic acid construct, which when introduced into a host cell, results in transcription and/or translation of a RNA or polypeptide, respectively.

In the case of expression of transgenes one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "IspS polynucleotide sequence" or "IspS gene".

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. *APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. A "comparison window", as used herein, includes reference to a segment of any one of the number of contiguous positions, e.g., 20 to 600, usually about 50 to about 200, more usually about 100 to about 150 in which a sequence may be compared to a reference sequence of the same number of contiguous positions after the two sequences are optimally aligned.

The term "substantial identity" in the context of polynucleotide or amino acid sequences means that a polynucleotide or polypeptide comprises a sequence that has at least 50% sequence identity to a reference sequence. Alternatively, percent identity can be any integer from 50% to 100%. Exemplary embodiments include at least: 55%, 57%, 60%, 65%, 70%, 75%, 80%, 85%, 90%, 95%, or 99% identity compared to a reference sequence using the programs described herein; preferably BLAST using standard parameters, as described below. Accordingly, IspS sequences of the invention include nucleic acid sequences that have substantial identity to SEQ ID NO:1 or SEQ ID NO:7 or to the IspS coding regions of SEQ ID NO:3 or SEQ ID NO:5. As noted above, IspS polypeptide sequences of the invention include polypeptide sequences having substantial identify to SEQ ID NO:2 or SEQ ID NO:8.

Polypeptides that are "substantially similar" share sequences as noted above except that residue positions that are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 55° C., 60° C., or 65° C. Such washes can be performed for 5, 15, 30, 60, 120, or more minutes.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. For example, an IspS polynucleotides, can also be identified by their ability to hybridize under stringency conditions (e.g., Tm ~40° C.) to nucleic acid probes having the sequence of SEQ ID NO:1 or SEQ ID NO:7. Such an IspS nucleic acid sequence can have, e.g., about 25-30% base pair mismatches or less relative to the selected nucleic acid probe. SEQ ID NO:1 is an exemplary IspS polynucleotide sequence. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The term "isolated", when applied to a nucleic acid or protein, denotes that the nucleic acid or protein is essentially free of other cellular components with which it is associated in the natural state. It is preferably in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest.

As used herein, "mass-culturing" refers to growing large quantities of microalgae, cyanobacteria, or photosynthetic or non-photosynthetic bacteria that have been modified to express an IspS gene. A "large quantity" is generally in the range of about 100 liters to about 1,500,000 liters, or more. In some embodiments, the organisms are cultured in large quantities in modular bioreactors, each having a capacity of about 1,000 to about 1,000,000 liters.

A "bioreactor" in the context of this invention is any enclosed large-capacity vessel in which microalgae, cyanobacteria or photosynthetic or non-photosynthetic bacteria are grown. A "large-capacity vessel" in the context of this invention can hold about 100 liters, often about 500 liters, or about 1,000 liters to about 1,000,000 liters, or more.

As used herein, "harvesting" volatile isoprene hydrocarbons refers to capturing and sequestering such hydrocarbons in a closed or contained environment.

IspS, Dxr, or Dxs Nucleic Acid Sequences

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel et al., eds., 1994-1999).

IspS nucleic acid and polypeptide sequences are known in the art. IspS genes have been isolated and sequenced from poplar and aspen (two related trees), and kudzu (a vine). The species involved and the sequences available in the NCBI database are given below by accession number, each of which is incorporated by reference:

*Populus alba* (white poplar) IspS mRNA for isoprene synthase; ACCESSION No AB198180;

*Populus tremuloides* (quaking aspen) isoprene synthase (IspS); ACCESSION No AY341431 (complete cds);

*Populus alba×Populus tremula* IspS mRNA; ACCESSION No AJ294819;

*Populus nigra* (Lombardy poplar) mRNA for isoprene synthase (IspS gene); ACCESSION No AM410988;

*Pueraria montana* var. *lobata* (kudzu vine) isoprene synthase (IspS); ACCESSION No AY316691 (complete cds.).

Examination of these IspS sequences reveals a high degree of nucleotide and amino acid sequence identities, for example, hybrid poplar and aspen cDNA sequences are 98% identical at the polypeptide and nucleotide level (see, e.g., Sharkey et al., *Plant Physiol.* 137:700-712, 1995). The aspen isoprene synthase nucleotide coding sequence is 65% identical to the kudzu gene, while the protein sequences (without the chloroplast transit peptide) are 57% identical.

The poplar IspS protein has a high-density of Cysteine and Histidine amino acids in the carboxy-terminal half of the protein. For example, considering the 591 amino acid sequence of the Cr-IspS protein (SEQ ID NO:4), cysteine moieties are found at positions 34, 326, 378, 413, 484, 505 and 559, i.e., six out of the seven cysteines are found in the lower 45% of the protein. Additional clustering of histidines in various positions of the C-terminal half of the protein is also observed. Cysteine and histidine amino acids are known to participate in proper folding and catalytic site structure of proteins and can be important components for enzyme activity. An alignment of four known IspS proteins showing the high conservation of Cys in the C-terminal part of the molecule is provided in FIG. 13. In one case, the kudzu protein has substituted an otherwise conserved Cys with Ser (Cys-509-Ser of the Alba or nigra or tremuloides) sequence in the clustal alignment in FIG. 13). Serine is a highly conservative substitution for cysteine, as the only difference between the two amino acids is a —OH group in the place of the —SH group. In fact, examination of the four IspS sequences reveals the additional property of many conserved Serines in the C-terminal half of the protein. Accordingly, in some embodiments, a nucleic acid for use in the invention encodes an IspS polypeptide that comprises the carboxyl-terminal 45% of SEQ ID NO:2 and retain the catalytic activity in converting DMAPP to isoprene. Other examples exist where a related protein in one microorganism, such as a green microalgae, lacks a substantial portion of the N-terminal portion of the protein (relative to the form of the protein present in another microorganism such as bacteria) without adverse effect on activity (see, e.g., Melis and Happe, *Plant Physiol.* 127:740-748, 2001). Accordingly, in some embodiments, an IspS nucleic acid for use in the invention encodes a polypeptide that comprises from about amino acid residue 330 through the C-terminus of SEQ ID NO:2 or SEQ ID NO:8. In some embodiments, the IspS polypeptide encoded by the IspS nucleic acid comprises from about amino acid residue 300 through the C-terminus of SEQ ID NO:2 or SEQ ID NO:8. In some embodiments, the IspS sequence can additionally lack the last 10, 15, or 20 residues of SEQ ID NO:2 or SEQ ID NO:8.

The transit peptide of the IspS protein includes, minimally, amino acids 1-37 for poplar and aspen and 1-45 for kudzu. On the basis of this analysis, the mature protein begins with the amino acid sequence "CSVSTEN. . . (SEQ ID NO:11) etc. IspS nucleic acid sequences for use in the invention need not include sequences that encode a transit polypeptide and further omit additional N-terminal sequence. For example, the Ss-IspS construct set forth in the EXAMPLES section lacks 52 amino acids from the encoding synthetic gene DNA. This has had no effect on IspS protein synthesis and accumulation.

In some embodiments of the invention, a nucleic acid sequence that encodes a poplar or aspen IspS polypeptide (e.g., SEQ ID NO:2) is used. In other embodiments, a nucleic acid sequence that encodes a kudzu IspS polypeptide (e.g., SEQ ID NO:8) is used. The IspS polypeptides encoded by the nucleic acids employed in the methods of the invention have the catalytic activity of converting DMAPP to isoprene. Typically, the level of activity is equivalent to the activity exhibited by a poplar or aspen IspS polypeptide (e.g., encoded by SEQ ID NO:1) or a natural kudzu IspS polypeptide (e.g., encoded by SEQ ID NO:7).

Exemplary Dxs and Dxr sequences include the nucleic acid and polypeptide Dxs and Dxr sequences disclosed in U.S. Patent Application Publication No. 20030219798, e.g., *Chlamydomonas* sequences. The Dxs and Dxr sequences of U.S. Patent Application Publication No. 20030219798 are herein incorporated by reference.

Isolation or generation of IspS, Dxr, or Dxs polynucleotide sequences can be accomplished by a number of techniques. Cloning and expression of such technique will be addressed in the context of IspS genes. However, the same techniques can be used to isolate and express Dxr or Dxs polynucleotides. For instance, oligonucleotide probes based on the sequences disclosed here can be used to identify the desired polynucleotide in a cDNA or genomic DNA library from a desired plant species. Such a cDNA or genomic library can then be screened using a probe based upon the sequence of a cloned IspS gene, e.g., SEQ ID NO:1 or SEQ ID NO:7. Probes may be used to hybridize with genomic DNA or cDNA sequences to isolate homologous genes in the same or different plant species.

Alternatively, the nucleic acids of interest can be amplified from nucleic acid samples using amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying an IspS gene from plant cells, e.g., poplar or another deciduous tree, can be generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). An exemplary PCR for amplifying an IspS nucleic acid sequence is provided in the examples.

The genus of IspS nucleic acid sequences for use in the invention includes genes and gene products identified and characterized by techniques such as hybridization and/or sequence analysis using exemplary nucleic acid sequences, e.g., SEQ ID NO:1 or SEQ ID NO:7 and protein sequences, e.g., SEQ ID NO:2 or SEQ ID NO:8.

Preparation of Recombinant Vectors

To use isolated sequences in the above techniques, recombinant DNA vectors suitable for transformation of green microalgae, cyanobacteria, and photosynthetic or non-photosynthetic bacterial cells, are prepared. Techniques for transformation are well known and described in the technical and scientific literature. For example, a DNA sequence encoding an IspS gene (described in further detail below), can be combined with transcriptional and other regulatory sequences which will direct the transcription of the sequence from the gene in the intended cells of the transformed algae, cyanobacteria, or bacteria. In some embodiments, an expression vector that comprises an expression cassette that comprises the IspS gene further comprises a promoter operably linked to the IspS gene. In other embodiments, a promoter and/or other regulatory elements that direct transcription of the IspS gene are endogenous to the microorganism and the expression cassette comprising the IspS gene is introduced, e.g., by homologous recombination, such that the heterologous IspS gene is operably linked to an endogenous promoter and is expression driven by the endogenous promoter.

Regulatory sequences include promoters, which may be either constitutive or inducible. In some embodiments, a promoter can be used to direct expression of IspS nucleic acids under the influence of changing environmental conditions. Examples of environmental conditions that may effect transcription by inducible promoters include anaerobic conditions, elevated temperature, or the presence of light. Promoters that are inducible upon exposure to chemicals reagents are also used to express IspS nucleic acids. Other useful inducible regulatory elements include copper-inducible regulatory elements (Mett et al., *Proc. Natl. Acad. Sci. USA* 90:4567-4571 (1993); Furst et al., *Cell* 55:705-717 (1988)); tetracycline and chlor-tetracycline-inducible regulatory elements (Gatz et al., *Plant J.* 2:397-404 (1992); Röder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., *EMBO J.* 11:1251-1259 (1992)). An inducible regulatory element also can be, for example, a nitrate-inducible promoter, e.g., derived from the spinach nitrite reductase gene (Back et al., *Plant Mol. Biol.* 17:9 (1991)), or a light-inducible promoter, such as that associated with the small subunit of RuBP carboxylase or the LHCP gene families (Feinbaum et al., *Mol. Gen. Genet.* 226:449 (1991); Lam and Chua, Science 248:471 (1990)), or a light.

In one example, a promoter sequence that is responsive to light may be used to drive expression of an IspS nucleic acid construct that is introduced into *Chlamydomonas* that is exposed to light (e.g., Hahn, *Curr Genet.* 34:459-66, 1999; Loppes, *Plant Mol Biol* 45:215-27, 2001; Villand, *Biochem J* 327:51-7), 1997. Other light-inducible promoter systems may also be used, such as the phytochrome/PIF3 system (Shimizu-Sato, *Nat Biotechnol* 20): 1041-4, 2002). Further, a promoter can be used that is also responsive to heat can be employed to drive expression in algae such as *Chlamydomonas* (Muller, *Gene* 111:165-73, 1992; von Gromoff, *Mol Cell Biol* 9:3911-8, 1989). Additional promoters, e.g., for expression in algae such as green microalgae, include the RbcS2 and PsaD promoters (see, e.g., Stevens et al., *Mol. Gen. Genet.* 251: 23-30, 1996; Fischer & Rochaix, *Mol Genet Genomics* 265:888-94, 2001).

In some embodiments, the promoter may be from a gene associated with photosynthesis in the species to be transformed or another species. For example such a promoter from one species may be used to direct expression of a protein in transformed algal cells or cells of another photosynthetic marine organism. Suitable promoters may be isolated from or synthesized based on known sequences from other photosynthetic organisms. Preferred promoters are those for genes from other photosynthetic species that are homologous to the photosynthetic genes of the algal host to be transformed. For example, a series of light harvesting promoters from the fucoxanthing chlorophyll binding protein have been identified in *Phaeodactylum tricornutum* (see, e.g., Apt, et al. *Mol. Gen. Genet.* 252:572-579, 1996). In other embodiments, a carotenoid chlorophyll binding protein promoter, such as that of peridinin chlorophyll binding protein, can be used.

In some embodiments, a promoter used to drive expression of a heterologous IspS gene is a constitutive promoter. Examples of constitutive strong promoters for use in microalgae include, e.g., the promoters of the atpA, atpB, and rbcL genes. Various promoters that are active in cyanobacteria are also known. These include promoters such as the (constitutive) promoter of the psbA3 gene in cyanobacteria and promoters such as those set forth in U.S. Patent Application Publication No. 20020164706, which is incorporated by reference. Other promoters that are operative in plants, e.g., promoters derived from plant viruses, such as the CaMV35S promoters, can also be employed in algae.

In some embodiments, promoters are identified by analyzing the 5' sequences of a genomic clone corresponding to an IspS gene. Sequences characteristic of promoter sequences can be used to identify the promoter.

A promoter can be evaluated, e.g., by testing the ability of the promoter to drive expression in plant cells, e.g., green algae, in which it is desirable to introduce an IspS expression construct.

A vector comprising IspS nucleic acid sequences will typically comprise a marker gene that confers a selectable phenotype on algae or bacterial cells. Such markers are known. For example, the marker may encode antibiotic resistance, such as resistance to kanamycin, G418, bleomycin, hygromycin, and the like. In some embodiments, selectable markers for use in *Chlamydomonas* can be markers that provide spectinomycin resistance (Fargo, *Mol Cell Biol* 19:6980-90, 1999), kanamycin and amikacin resistance (Bateman, *Mol Gen Genet.* 263:404-10, 2000), zeomycin and phleomycin resistance (Stevens, *Mol Gen Genet.* 251:23-30, 1996), and paromomycin and neomycin resistance (Sizova, *Gene* 277: 221-9, 2001).

IspS nucleic acid sequences of the invention are expressed recombinantly in microorganisms, e.g., microalgae, cyanobacteria, or photosynthetic or non-photosynthetic bacteria. As appreciated by one of skill in the art, expression constructs can be designed taking into account such properties as codon usage frequencies of the organism in which the IspS nucleic acid is to be expressed. Codon usage frequencies can be tabulated using known methods (see, e.g., Nakamura et al. *Nucl. Acids Res.* 28:292, 2000). Codon usage frequency tables, including those for microalgae and cyanobacteria, are also available in the art (e.g., in codon usage databases of the Department of Plant Genome Research, Kazusa DNA Research Institute (www.kazusa.or.jp/codon).

Cell transformation methods and selectable markers for bacteria and cyanobacteria are well known in the art (Wirth, *Mol Gen Genet.* 1989 March; 216(1):175-7; Koksharova, *Appl Microbiol Biotechnol* 2002 February; 58(2):123-37; Thelwell). Transformation methods and selectable markers for use in bacteria are well known (see, e.g., Sambrook et al, supra).

In microalage, e.g., green microalgae, the nuclear, mitochondrial, and chloroplast genomes are transformed through a variety of known methods, including by microparticle bombardment, or using a glass bead method (see, e.g., Kindle, *J Cell Biol* 109:2589-601, 1989; Kindle, *Proc Natl Acad Sci USA* 87:1228-32, 1990; Kindle, *Proc Natl Acad Sci USA* 88:1721-5, 1991; Shimogawara, *Genetics* 148:1821-8, 1998; Boynton, *Science* 240:1534-8, 1988; Boynton, *Methods Enzymol* 264:279-96, 1996; Randolph-Anderson, *Mol Gen Genet.* 236:235-44, 1993). In some embodiments, an IspS gene is introduced into the chloroplast of a microalgae. In other embodiments, an IspS gene is introduced into the nucleus.

The techniques described herein for obtaining and expressing IspS nucleic acid sequences in microalgae, cyanobacteria or photosynthetic or non-photosynthetic bacteria can also be employed to express Dxr or Dxs nucleic acid sequences.

Microorganisms that can be Targeted

IspS can be expressed in any number of microalgae, e.g., green algae, or cyanobacteria, or photosynthetic or non-photosynthetic bacteria where it is desirable to produce isoprene. Transformed microalgae, cyanobacteria, or bacteria (photosynthetic bacteria or non-photosynthetic bacteria) that express a heterologous IspS gene are grown under mass culture conditions for the production of hydrocarbons, e.g., to be used as a fuel source or as feedstock in synthetic chemistry. The transformed organisms are growth in bioreactors or fermentors that provide an enclosed environment to contain the hydrocarbons. In typical embodiments for mass culture, the microalgae, cyanobacteria, or bacteria are grown in enclosed reactors in quantities of at least about 500 liters, often of at least about 1000 liters or greater, and in some embodiments in quantities of about 1,000,000 liters or more.

In some embodiments, IspS is expressed in microalgae. Algae, alga or the like, refer to plants belonging to the subphylum Algae of the phylum Thallophyta. The algae are unicellular, photosynthetic, oxygenic algae and are non-parasitic plants without roots, stems or leaves; they contain chlorophyll and have a great variety in size, from microscopic to large seaweeds. Green algae, which are single cell eukaryotic organisms of oxygenic photosynthesis endowed with chlorophyll a and chlorophyll b belonging to Eukaryota—Viridiplantae—Chlorophyta—Chlorophyceae, are often a preferred target. For example, IspS can be expressed in *C. reinhardtii*, which is classified as Volvocales—Chlamydomonadaceae. Algae strains that may be used in this invention include, e.g., *Chlamydomonas reinhardtii, Scenedesmus obliquus, Chlorella vulgaris, Botryococcus braunii, Botryococcus sudeticus, Dunaliella salina,* and *Haematococcus pluvialis.*

Methods of mass-culturing algae are known. For example, algae can be grown in high density photobioreactors (see, e.g., Lee et al., *Biotech. Bioengineering* 44:1161-1167, 1994; Chaumont, *J Appl. Phycology* 5:593-604, 1990), bioreactors such as those for sewage and waste water treatments (e.g., Sawayama et al., *Appl. Micro. Biotech.*, 41:729-731, 1994; Lincoln, *Bulletin De L'institut Oceangraphique (Monaco),* 12:109-115, 1993), mass-cultured for the elimination of heavy metals from contaminated water (e.g., Wilkinson, *Biotech. Letters,* 11:861-864, 1989), mass-cultured for the production of β-carotene (e.g., Yamaoka, *Seibutsu-Kogaku Kaishi,* 72:111-114, 1994), hydrogen (e.g., U.S. Patent Application Publication No. 20030162273), and pharmaceutical compounds (e.g., Cannell, 1990), as well as nutritional supplements for both humans and animals (Becker, 1993, "Bulletin De L'institut Oceanographique (Monaco), 12, 141-155) and for the production of other compounds of nutritional value.

Conditions for growing IspS-expressing algae or bacteria for the exemplary purposes illustrated above are known in the art (see, e.g., the exemplary references cited herein). Volatile isoprene hydrocarbons produced by the modified microorganisms can be harvested using known techniques. Isoprene hydrocarbons are not miscible in water and they rise to and float at the surface of the microorganism growth medium. They are siphoned off from the surface and sequestered in suitable containers. In addition, and depending on the prevailing temperature during the mass cultivation of the microorganisms, isoprene can exist in vapor form above the water medium in the bioreactor container (isoprene boiling temperature T=34° C.). Isoprene vapor is piped off the bioreactor container and condensed into liquid fuel form upon cooling or low-level compression.

EXAMPLES

The examples described herein are provided by way of illustration only and not by way of limitation. Those of skill in the art will readily recognize a variety of non-critical parameters that could be changed or modified to yield essentially similar results.

Example 1

Design and Expression of Novel Cr-IspS Gene for Isoprene Hydrocarbon Production in Microalgae A codon-adjusted synthetic DNA construct was generated based on the known nuclear-encoded "isoprene synthase" IspS protein sequence of *Populus alba* (poplar). This amino acid sequence (SEQ ID NO:2) was used as a template for the de novo design of an IspS DNA sequence for expression of the gene in the chloroplast of model microalga *Chlamydomonas reinhardtii*. For the purposes of this invention, this gene has been termed Cr-IspS. Features of this gene included: (1) Codon usage was different from that of poplar and specifically selected to fit the codon usage of the *Chlamydomonas reinhardtii* chloroplast; (2) The poplar chloroplast targeting sequence of the protein was omitted from the design of the new Cr-IspS gene. (3) Three copies of a codon optimized gene encoding the hemagglutinin (HA) epitope tag were fused upstream of the IspS gene.

The Cr-IspS DNA sequence (SEQ ID NO:3) was designed to encode for the isoprene synthase protein (SEQ ID NO:4) specifically in the chloroplast of microalgae, e.g., *Chlamydomonas reinhardtii*. Codon usage adjustments for gene expression in the chloroplast of *Chlamydomonas* were made on the basis of the codon usage table for the *Chlamydomonas reinhardtii* chloroplast 6803, listed in the following URL: http://www.bio.net/bionet/mm/chlamy/1997-March/000843.html.

SEQ ID NO:4 also contains three copies of the hemagglutinin tag, which are underlined in the N-terminal side of the sequence. Restriction enzyme recognition sites were introduced at the ends of the Cr-IspS DNA sequence to facilitate cloning of the gene, and the entire sequence was synthesized and cloned in a carrier-plasmid.

Figure 4:
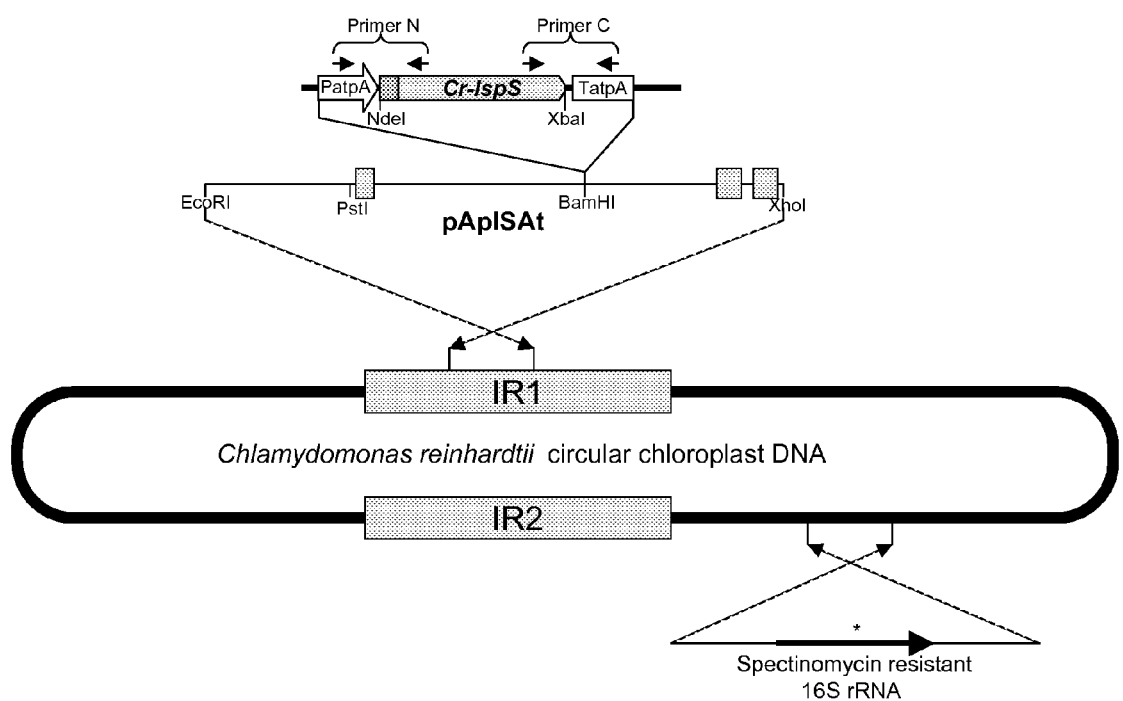
FIG. 4. Co-transformation and homologous recombination of green algal, e.g. *Chlamydomonas reinhardtii*, chloroplast DNA with novel Cr-IspS gene. This construct contains the atpA promoter (PatpA), fused to the 5' UTR end of a codon optimized three-copy hemagglutinin (HA) epitope tag DNA. The DNA sequence is followed by the Cr-IspS coding region, followed by the atpA 3' UTR.

A transgenic *Chlamydomonas reinhardtii* chloroplast was generated that expressed the codon-optimized recombinant isoprene synthase gene (Cr-IspS). This was accomplished by constructing a chimeric gene (FIG. 4 top, Cr-IspS) containing the atpA promoter (PatpA), fused to the 5'UTR end of a codon optimized three-copy hemagglutinin (HA) epitope tag DNA (FIG. 4). This DNA sequence was followed by the Cr-IspS coding region (FIG. 4), followed by the atpA 3'UTR (FIG. 4, TatpA). Integration of the constructed chimeric gene into the *Chlamydomonas reinhardtii* chloroplast genome was achieved using biolistic transformation and homologous recombination, requiring sequence homology between the transforming vector and the chloroplast genome (Boynton et al., *Science,* 240:1534-1538, 1988). For this purpose, the vector p322 was employed, which contains a partial *C. reinhardtii* chloroplast genome for the target of homologous recombination (Franklin et al., *Plant J.,* 30:733-744, 2002). As shown in the diagram of FIG. 4, the chimeric Cr-IspS gene was ligated into the BamHI site of p322 to generate plasmid pApISAt. The pApISAt construct was co-transformed into the *C. reinhardtii* strain CC503 chloroplast by means of particle bombardment (Boynton et al., *Science,* 240:1534-1538, 1988), along with plasmid p228, containing a modified 16S ribosomal gene conferring spectinomycin resistance (Franklin et al., *Plant J.,* 30:733-744, 2002). Primers N and C in FIG. 4 mark the annealing location of primers that were used for the subsequent PCR screening among isolated spectinomycin resistant transformants.

Figure 5:
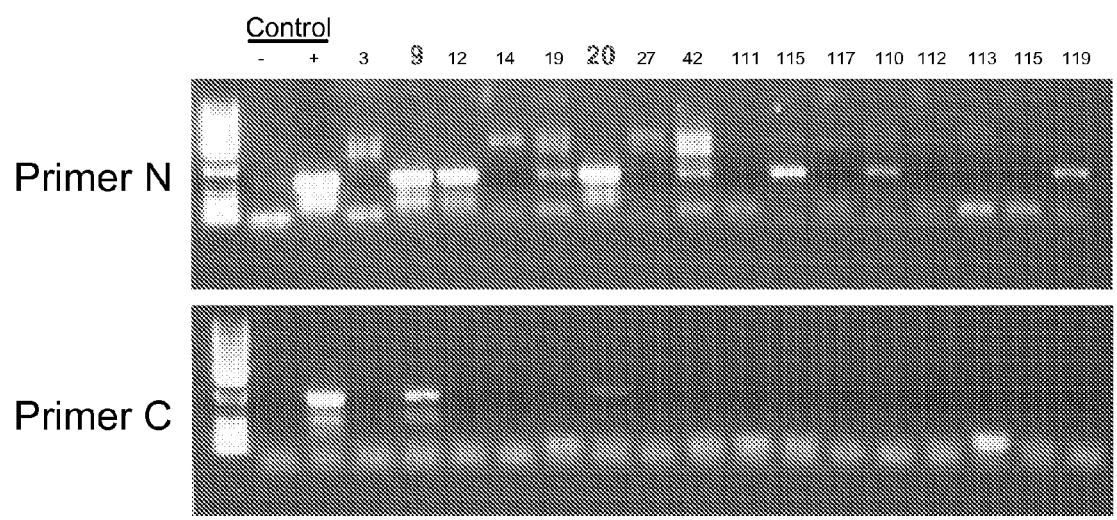
FIG. 5. Screening for *C. reinhardtii* IspS (Cr-IspS) transformants by genomic DNA PCR. Primers N and C represent the primer set used for amplification, and their annealing locations are shown in FIG. 4.

FIG. 5 provides an example of the genomic PCR screening analysis of primary transformants that were selected on media containing spectinomycin for the presence of either N- or C-terminal regions of the chimeric Cr-IspS gene in order to screen for *C. reinhardtii* Cr-IspS transformants. Over one hundred spectinomycin resistant transformant colonies of *Chlamydomonas reinhardtii* were isolated and tested, among which two independent lines (#9 and #20) were found to unequivocally contain the stably integrated Cr-IspS gene in their chloroplast DNA. A spectinomycin resistant transformant (#7, not shown) was used as negative control for the PCR analysis and the pApISAt plasmid served as a template for the positive control. Primers N and C represent the primer set used for amplification, and their annealing locations are shown in FIG. 4.

Figures 6A, 6B:
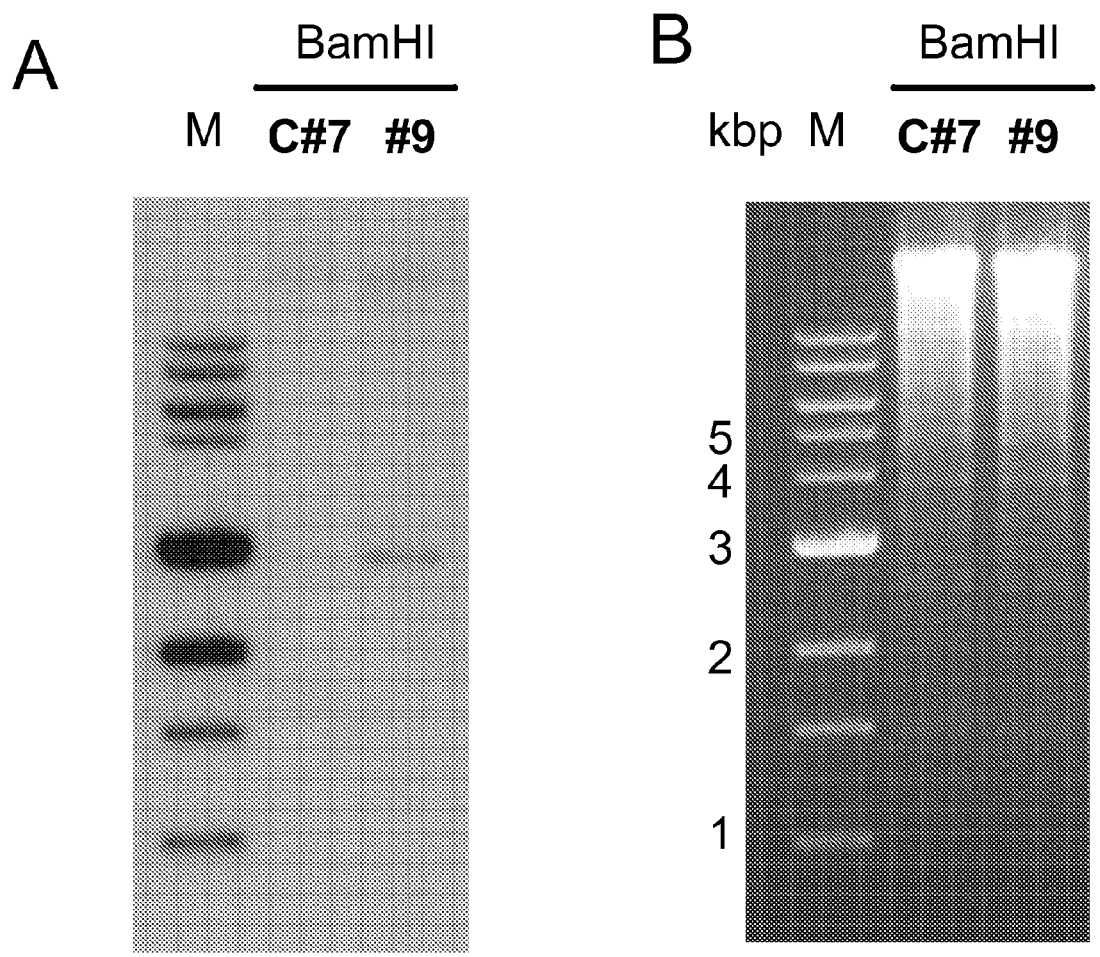
FIG. 6. A. Cr-IspS transgene integrity tested by genomic DNA Southern blot analysis. Filters probed with the Cr-IspS DNA probe. Hybridization with a radio-labeled NdeI/XbaI fragment of the Cr-IspS coding region identified a 3.0 kbp band exclusively in the Cr-IspS transformant line #9, whereas no detectable band could be observed in the control line #7 lane. B. Ethidium bromide staining to test for equal amounts of DNA loading in A.

Genomic DNA from *Chlamydomonas reinhardtii* control (#7) and the putative Cr-IspS transformant line #9 were digested with BamHI, separated on an Agarose gel, and subjected to Southern blot analysis in order to test for Cr-IspS transgene integrity. Hybridization with a radio-labeled NdeI/XbaI fragment of the Cr-IspS coding region identified a ~3.0 kbp band exclusively in the Cr-IspS transformant line #9, whereas no detectable band could be observed in the control line #7 lane (FIG. 6A). These results validated the stable integration of Cr-IspS in the chloroplast genome of *Chlamydomonas reinhardtii* transformant line #9, and are consistent with the results of the PCR analysis (FIG. 5). Ethidium bromide staining of the Agarose gel (FIG. 6B) tested for the equal amount of DNA loading. Similar results were obtained with the Cr-IspS transformant line #20 (not shown).

Figure 7A:
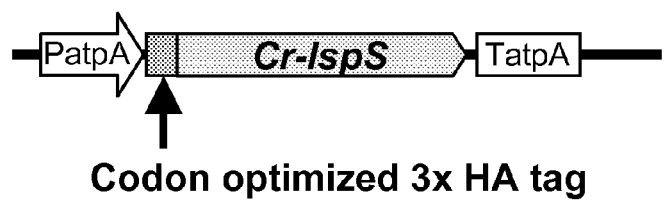
FIG. 7. A. Schematic representation of the Codon optimized 3×HA tagged Cr-IspS gene. B. Validation of Cr-IspS gene expression. Soluble protein fractions, which correspond to 10 or 20 μg chlorophyll, were subjected to SDS-PAGE and Western blot analysis with specific polyclonal anti-HA antibodies.
Figure 7B:
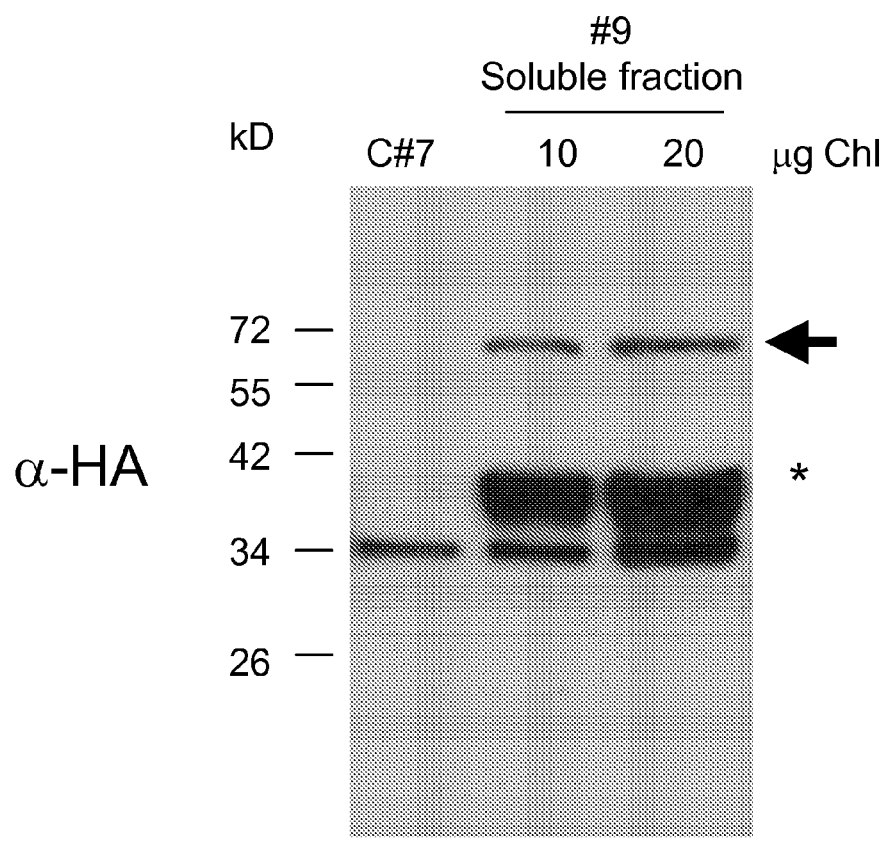

Cr-IspS protein accumulation in the *Chlamydomonas reinhardtii* transgenic line #9 was verified by Western blot analysis (FIG. 7) in order to demonstrate Cr-IspS gene expression. Anti-HA tag antibody (α-HA) was used to assay for the presence of the recombinant Cr-IspS protein and its cellular concentration. Three copies of hemagglutinin (HA) tag were introduced into a position preceding the Cr-IspS gene that encodes the mature protein (FIG. 7A), to serve as a convenient epitope for the detection of Cr-IspS protein accumulation. *Chlamydomonas reinhardtii* cells were concentrated to $500 \times 10^6$ cells/ml in 50 mM HEPES buffer (pH7.0) and broken by glass bead agitation for 5 min to release the soluble fraction of chloroplast. Soluble protein fractions, which correspond to 10 or 20 μg chlorophyll, were subjected to SDS-PAGE and Western blot analysis with specific polyclonal anti-HA antibodies. A clear antibody-protein cross-reaction was observed at about the 67 kD band in the lanes loaded with sample from the *Chlamydomonas reinhardtii* transformant line #9, but not in the control (C #7) (FIG. 7B). In addition, antibody-protein cross-reactions were observed at about 38 kD, indicated by asterisk in FIG. 5B. Accumulation of Cr-IspS protein as a 38 kD band might indicate a premature termination of Cr-IspS mRNA translation, or a specific degradation activity over the recombinant protein. There was no detectable 67 kD or 38 kD bands in the control lane (C #7). The apparent cross-reaction corresponding to a 34 kD protein is probably a non-specific binding of the primary or secondary antibody to a *Chlamydomonas reinhardtii* protein. Expression of the Cr-IspS protein was also detected in transformant line #20 (not shown).

Example 2

Design and Expression of a Ss-IspS Gene for Isoprene Hydrocarbon Production in Cyanobacteria In order to express isoprene hydrocarbon production in cyanobacteria, a codon-adjusted synthetic DNA construct was generated, based on the known isoprene synthase IspS protein sequence of *Populus alba* (poplar). This amino acid sequence was used as a template for the de novo design of an IspS DNA sequence for expression of the gene in cyanobacteria, e.g., *Synechocystis* sp. Codon usage adjustments for gene expression in cyanobacteria were made on the basis of the codon usage Table for *Synechocystis* PCC 6803, listed in the following URL: http://gib.genes.nig.ac.jp/single/codon/main.php?spid=Syne_PCC6803.

Figure 8:
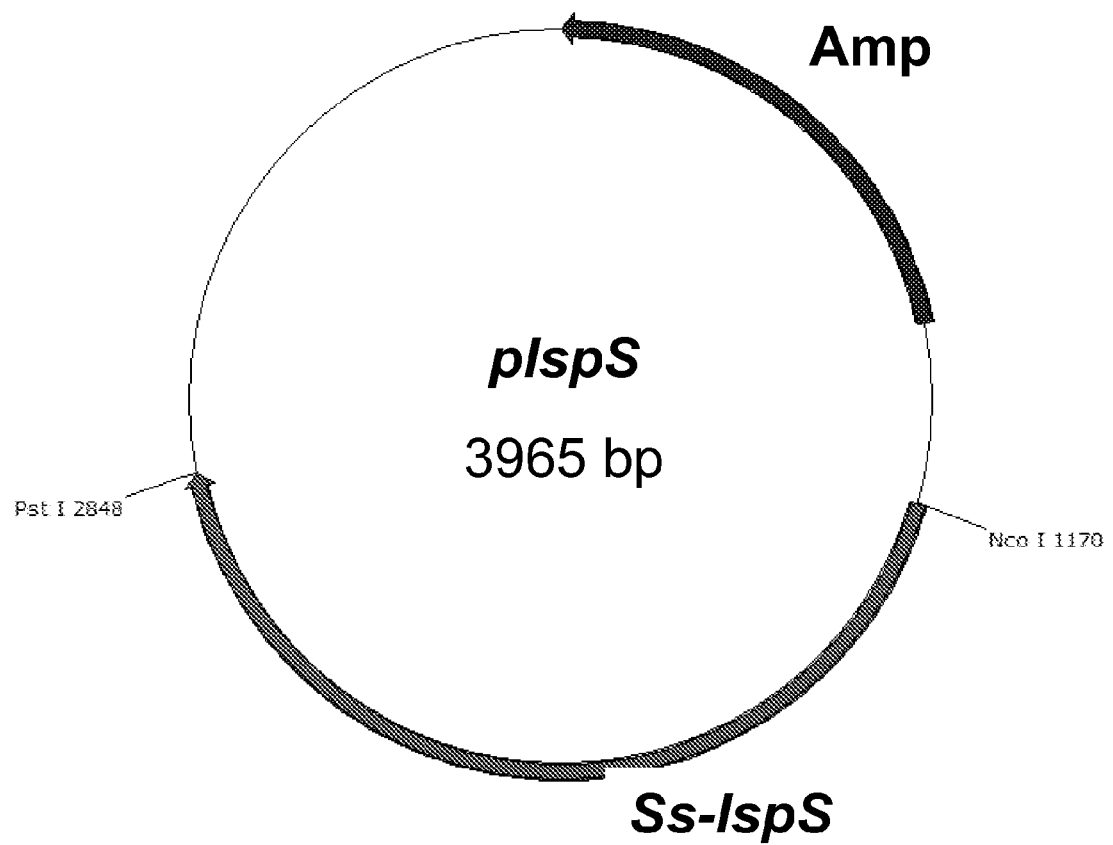
FIG. 8. Components and structure of the pIspS plasmid. Novel isoprene synthase gene (Ss-IspS) with codon usage designed for expression in cyanobacteria, e.g. *Synechocystis*, which includes an Ampicillin resistance gene. The novel Ss-IspS DNA sequence was designed on the basis of the amino acid sequence template of the poplar isoprene synthase protein, with criteria designed to conform to the *Synechocystis* codon preferences. Restriction sites were introduced to facilitate cloning. The novel Ss-IspS DNA sequence was synthesized and cloned into plasmid pIspS for propagation in *E. coli*.
Figure 9:
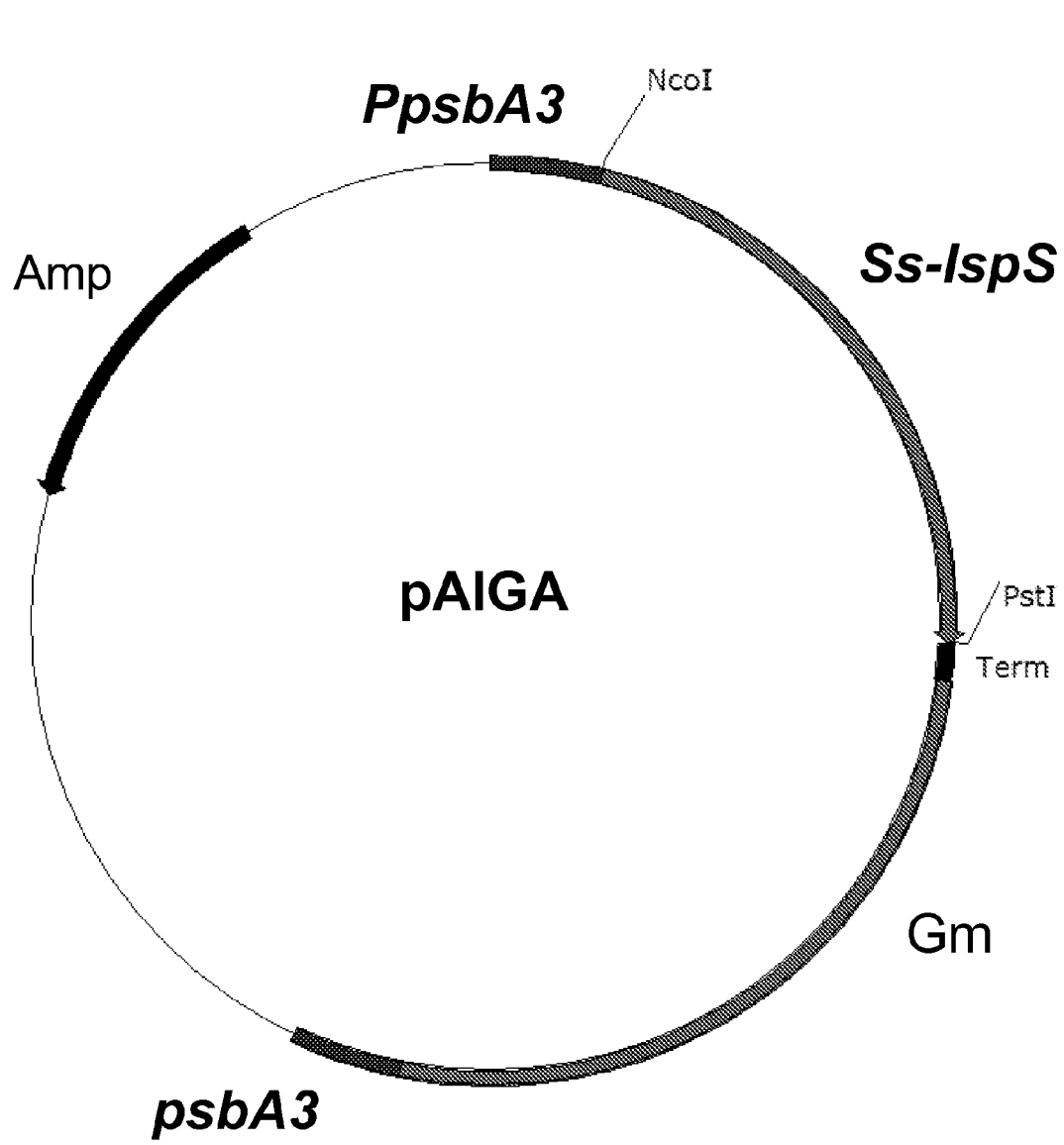
FIG. 9. Construction of pAIGA plasmid for transformation of cyanobacteria, e.g., *Synechocystis*. Flanking sequences from the psbA3 gene of *Synechocystis* were used for homologous recombination of the plasmid and to subsequently drive expression of the Ss-IspS gene with a strong promoter. A Gentamycin resistance cassette was introduced in the plasmid at the 3' end of the Ss-IspS gene to serve as selectable marker. The Ss-IspS gene was cloned between the NcoI and PstI restriction sites.

The codon-adjusted gene is referred to herein as Ss-IspS. Features of this gene include: (1) Codon usage was different from that of poplar and specifically selected to fit the codon usage of *Synechocystis*; (2) The poplar chloroplast targeting sequence of the protein was omitted from the design of the new Ss-IspS gene. The DNA sequence was designed to encode the isoprene synthase protein specifically in cyanobacteria, e.g. *Synechocystis*. The first underlined sequence of SEQ ID NO:5 represents the (reverse compliment) beta-lactamase gene, whereas the second underlined sequence is the Ss-IspS DNA. Additionally, the italicized sequences are start and stop codons, and the bold sequences are cloning restriction sites. Restriction enzyme recognition sites were introduced at the ends of the newly designed Ss-IspS DNA sequence to facilitate cloning of the gene, and the entire sequence was synthesized and cloned in a carrier-plasmid (FIG. 8).

The codon-optimized, length-adjusted and chemically-synthesized Ss-IspS gene was cloned downstream of the psbA3 promoter region of *Synechocystis*, in frame with the ATG start codon of the psbA3 gene. The Ss-IspS gene was followed by a transcriptional terminator and a gentamicin resistance cassette and, thereafter, by the *Synechocystis* sequence immediately downstream of psbA3 gene (FIG. 8).

Figure 10:
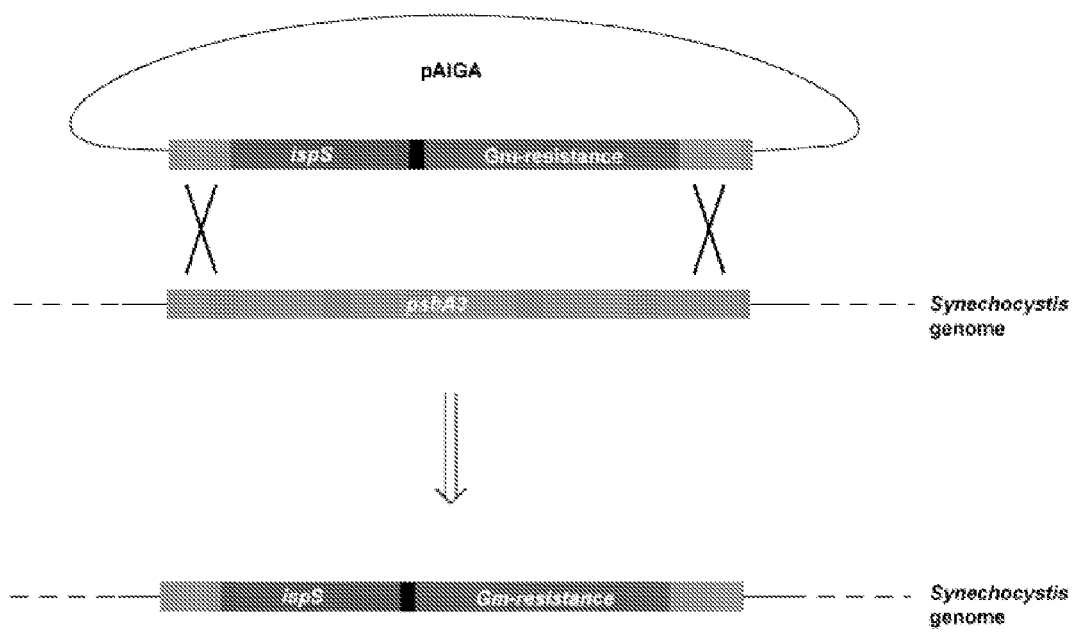
FIG. 10. Double homologous recombination. Schematic showing the principle of *Synechocystis* sp. transformation by double-homologous recombination and replacement of the native psbA3 gene by the Ss-IspS Gm-resistance construct.

This new construct allowed for homologous recombination, i.e., insertion of the Ss-IspS DNA sequence into the *Synechocystis* genome by replacement of the endogenous psbA3 gene via double homologous recombination (FIG. 10). Selection of *Synechocystis* transformants could be made using gentamicin (Gm) as the selectable marker, and the strong psbA3 promoter drove expression of the Ss-IspS gene.

In order to transform *Synechocystis* with the Ss-IspS construct, *Synechocystis* sp. cells were grown in a basic BG11 growth medium in the presence of 5 mM glucose, until cell density reached about $50 \times 10^6$ cells ml$^{-1}$ (OD$_{730}$=0.5). Cells were then harvested and concentrated to $10^{10}$ cells ml$^{-1}$, mixed with the pAIGA plasmid for transformation and incubated for 4-6 h prior to spreading of the mixture onto filters on top of BG11-containing agar plates, also containing 0.5 µg/ml Gm, 0.3% sodium thiosulfate, and 10 mM TES-NaOH, pH8.0.

The Petri plates were kept under low light intensity for 1-2 days and thereafter moved to normal growth conditions. Filters were transferred to fresh Gm-containing plates once a week. es that formed in the presence of the Gm selectable marker were isolated and re-streaked on fresh filters, followed by transfer to liquid BG11 growth media under continued selective conditions in the presence of Gm.

Example 3

Expression of His-tagged IspS in *Escherichia coli*

In order to construct the vector for expression of His-tagged IspS gene in *E. coli*, Ss-IspS DNA, codon optimized for expression in cyanobacteria, was amplified by PCR using primers:

```
IspS_F_NdeI,
5'-CTGGGTCATATGGAAGCTCGACGAA-3'    (SEQ ID NO: 12), and

IspS_R_HindIII,
5'-ATGGAAAACCTGAAGCTTTTAACGTTCAA-3' (SEQ ID NO: 13),
```

Figure 11:
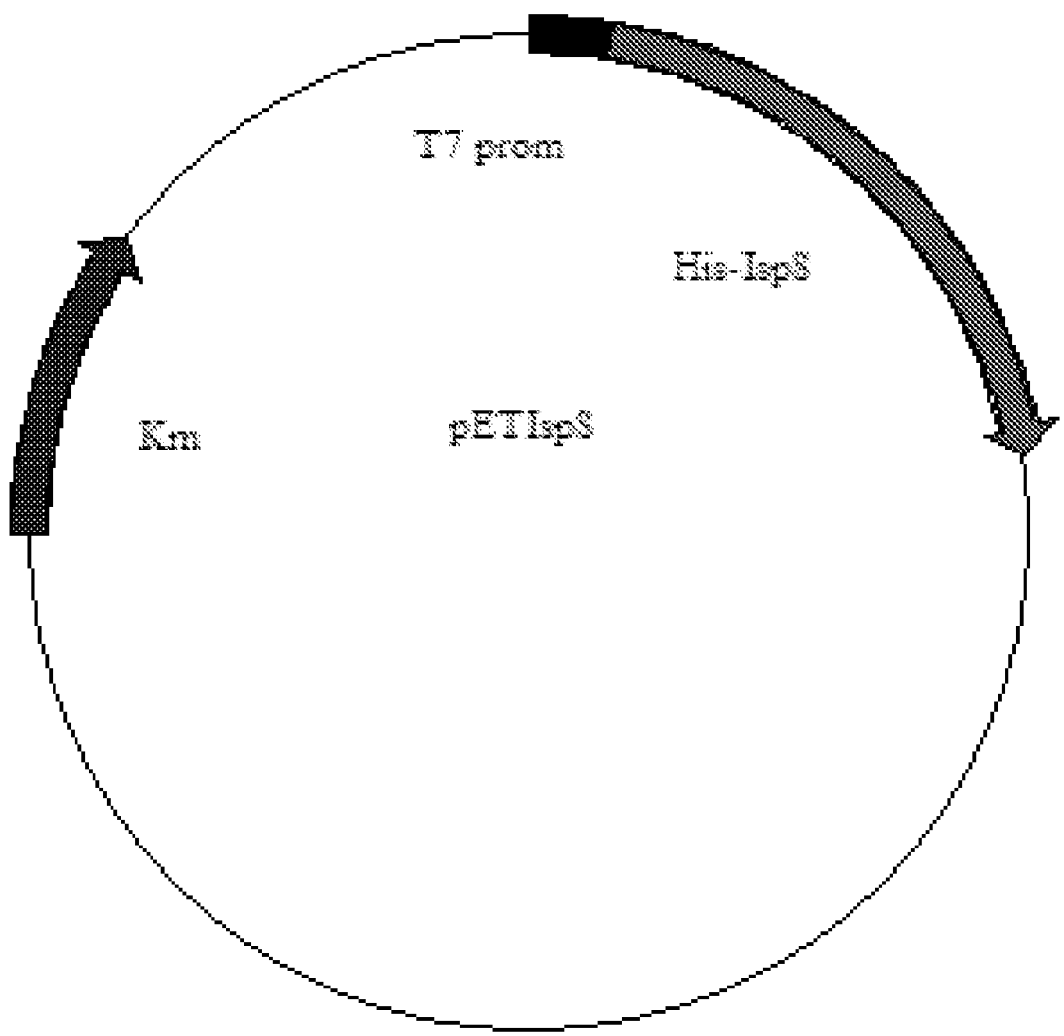
FIG. 11. Structure of a His-tagged Ss-IspS-containing plasmid for recombinant protein over-expression in bacteria, e.g. *Escherichia coli*. The N-terminal histidine-tag was introduced to facilitate purification of recombinant protein. *E. coli* expression was induced upon addition of IPTG to the liquid cell culture.

NO:13), introducing an Nde I-site and a Hind III-site in the 5' and 3' end of the gene, respectively. These sites were used to clone the gene into the pET1529 expression vector forming vector pETIspS, which carries a His-tag in the N-terminal end of the protein (FIG. 11).

Figure 12:
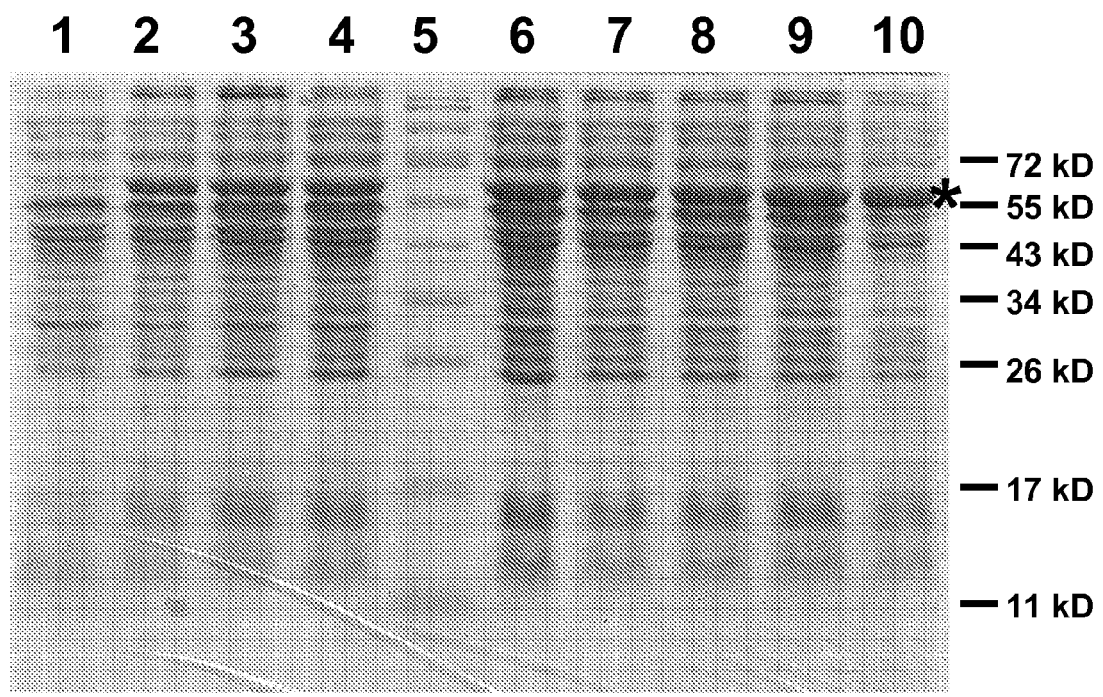
FIG. 12. Evidence of expression of the His-tagged Ss-IspS recombinant protein in bacteria, e.g. *E. coli*. Coomassie-stained SDS-PAGE of electrophoretically separated total protein from cell extracts of *E. coli* carrying the pETIspS plasmid. Lane 1: Non-induced control culture. Lanes 2-4 and 6-10: Induced *E. coli* cultures. Lane 5: Molecular weight protein size markers.

In order to demonstrate recombinant His-tagged Ss-IspS expression in *Escherichia coli, E. coli* bacteria were transformed with the pETIspS plasmid, which contains the Ss-IspS gene and a His-tag-encoding DNA in the 5' end of the Ss-IspS gene. Successful expression of this His-Ss-IspS gene in *E. coli* was induced upon addition of 0.1 mM IPTG to the liquid cell culture. Cells were harvested and their protein content was analyzed by SDS-PAGE and Coomassie staining (FIG. 12). It was demonstrated that all clones carrying the pETIspS plasmid were expressing the ~65 kD His-Ss-IspS protein (FIG. 12, ~65 kD band).

A similar undertaking and demonstration of expression of the IspS gene and accumulation of the recombinant IspS protein in bacteria, e.g. *Escherichia coli*, was successfully conducted with the Cr-IspS gene, codon-optimized for expression in unicellular green algae, e.g. *Chlamydomonas reinhardtii* (results not shown).

All publications, accession numbers, and patent applications cited in this specification are herein incorporated by reference as if each individual publication or patent application were specifically and individually indicated to be incorporated by reference.

Exemplary IspS Sequences

```
SEQ ID NO: 1 Populus alba cDNA for isoprene synthase, Accession
No. AB198180
    1 atggcaactg aattattgtg cttgcaccgt ccaatctcac tgacacacaa acttttcaga 61 aatcccttac ctaaagtcat ccaggccact cccttaactt tgaaactcag atgttctgta 121 agcacagaaa acgtcagctt cacagaaaca gaaacagaag ccagacggtc tgccaattat 181 gaaccaaata gctgggatta tgattatttg ctgtcttcag acactgacga atcgattgag 241 gtatacaaag acaaggccaa aaagctggag gctgaggtga gaagagagat taacaatgaa 301 aaggcagagt ttttgactct gcttgaactg atagataatg tccaaaggtt aggattgggt 361 taccggttcg agagtgacat aagggggagcc cttgatagat ttgtttcttc aggaggattt 421 gatgctgtta caaaaactag ccttcatggt actgctctta gcttcaggct tctcagacag 481 catggttttg aggtctctca agaagcgttc agtggattca aggatcaaaa tggcaatttc 541 ttggaaaacc ttaaggagga catcaaggca atactaagcc tatatgaagc ttcatttctt 601 gcattagaag gagaaaatat cttggatgag gccaaggtgt ttgcaatatc acatctaaaa 661 gagctcagcg aagaaaagat tggaaaagag ctggccgaac aggtgaatca tgcattggag 721 cttccattgc atcgcaggac gcaaagacta gaagctgttt ggagcattga agcataccgt
```

```
 781 aaaaaggaag atgcaaatca agtactgcta gaacttgcta tattggacta caacatgatt 841 caatcagtat accaaagaga tcttcgcgag acatcaaggt ggtggaggcg agtgggtctt 901 gcaacaaagt tgcattttgc tagagacagg ttaattgaaa gcttttactg ggcagttgga 961 gttgcgttcg agcctcaata cagtgattgc cgtaattcag tagcaaaaat gttttcattt 1021 gtaacaatca ttgatgatat ctatgatgtt tatggtactc tggacgagtt ggagctattt 1081 acagatgctg ttgagagatg ggatgttaat gccatcaatg atcttccgga ttatatgaag 1141 ctctgcttcc tagctctcta caacactatc aatgagatag cttatgacaa tctgaaggac 1201 aagggggaaa acattcttcc atacctaaca aaagcgtggg cagatttatg caatgcattc 1261 ctacaagaag caaaatggtt gtacaataag tccacaccaa catttgatga ctatttcgga 1321 aatgcatgga atcatcctc agggcctctt caactagttt ttgcctactt tgccgtggtt 1381 caaacatca agaaagagga aattgaaaac ttacaaaagt atcatgatac catcagtagg 1441 ccttcccaca tctttcgtct ttgcaacgac ctggcttcag catcggctga gatagagaga 1501 ggtgaaacag cgaattctgt atcatgctac atgcgtacaa aaggcatttc tgaggagctt 1561 gctactgaat ccgtaatgaa cttgatcgac gaaacctgga aaagatgaa caaagaaaag 1621 cttggtggct ctttgtttgc aaaacctttt gtcgaaacag ctattaacct tgcacggcaa 1681 tcccattgca cttatcataa cggagatgcg catacttcac cagacgagct aactaggaaa 1741 cgtgtcctgt cagtaatcac agagcctatt ctacccttg agagataa
```

SEQ ID NO:2 *Populus alba* polypeptide sequence for isoprene synthase (from Accession No. AB198180). The underlined portion of the protein denotes a chloroplast transit peptide.

<u>MATELLCLHRPISLTHKLFRNPLPKVIQATPLTLKLR</u>CSVSTENVSFTETETEARRSANYEPNSWDYDYL

LSSDTDESIEVYKDKAKKLEAEVRREINNEKAEFLTLLELIDNVQRLGLGYRFESDIRGALDRFVSSGGF

DAVTKTSLHGTALSFRLLRQHGFEVSQEAFSGFKDQNGNFLENLKEDIKAILSLYEASFLALEGENILDE

AKVFAISHLKELSEEKIGKELAEQVNHALELPLHRRTQRLEAVWSIEAYRKKEDANQVLLELAILDYNMI

QSVYQRDLRETSRWWRRVGLATKLHFARDRLIESFYWAVGVAFEPQYSDCRNSVAKMFSFVTIIDDIYDV

YGTLDELELFTDAVERWDVNAINDLPDYMKLCFLALYNTINEIAYDNLKDKGENILPYLTKAWADLCNAF

LQEAKWLYNKSTPTFDDYFGNAWKSSSGPLQLVFAYFAVVQNIKKEEIENLQKYHDTISRPSHIFRLCND

LASASAEIARGETANSVSCYMRTKGISEELATESVMNLIDETWKKMNKEKLGGSLFAKPFVETAINLARQ

SHCTYHNGDAHTSPDELTRKRVLSVITEPILPFER

SEQ ID NO: 3 Cr-IspS gene and hemagglutinin tag for transformation/expression in unicellular green algae. The IspS nucleotide sequence starts with the underlined "TGT" codon.

<u>ATG</u>TATCCTTATGATGTTCCAGACTACGCAGGTTATCCTTATGATGTACCAGACTATGCAGGTTATCCTT

ACGATGTACCTGATTACGCTGGTCCATGG<u>TGT</u>TCTGTTAGTACTGAAAATGTTTCATTTACTGAAACAGA

AACAGAAGCACGTAGATCAGCAAATTATGAGCCAAATAGTTGGGATTATGACTATTTATTATCTAGTGAT

ACAGATGAATCTATTGAAGTATATAAAGATAAAGCAAAAAAATTAGAAGCAGAAGTACGTCGTGAAATTA

ATAACGAAAAGCAGAATTTCTTACTTTATTAGAATTAATTGATAATGTACAACGTTTAGGTTTAGGTTA

TCGTTTTGAATCAGACATTCGTGGTGCATTAGATCGTTTTGTATCAAGTGGTGGTTTTGATGCTGTTACA

AAAACTAGTTTACATGGTACTGCTTTAAGTTTTCGTTTACTTCGTCAACATGGTTTTGAAGTAAGTCAAG

AAGCTTTTTCTGGTTTTAAAGATCAAAATGGTAATTTCTTAGAAAATTTAAAAGAAGATATTAAAGCTAT

TTTAAGTTTATACGAAGCATCATTTTTAGCTTTAGAAGGTGAAAATATTTTAGATGAAGCTAAAGTATTT

GCTATTTCTCACTTAAAAGAATTATCAGAAGAAAAAATTGGTAAAGAATTAGCTGAACAAGTAAACCATG

CATTAGAATTACCATTACATCGTCGTACACAACGTTTAGAAGCAGTTTGGTCTATTGAAGCTTATCGTAA

-continued

```
AAAAGAAGATGCTAATCAAGTTTTATTAGAATTAGCAATTTTAGATTATAATATGATTCAATCAGTATAC

CAACGTGATTTACGTGAAACAAGTCGTTGGTGGCGTCGTGTAGGTTTAGCTACTAAATTACATTTTGCTC

GTGATCGTTTAATTGAAAGTTTTTATTGGGCAGTTGGTGTAGCTTTTGAACCACAATATTCAGATTGTCG

TAATTCAGTTGCAAAAATGTTTTCATTTGTAACTATTATTGATGATATTTATGATGTTTACGGTACATTA

GATGAATTAGAATTATTCACTGATGCAGTAGAACGTTGGGATGTTAATGCTATTAATGATTTACCAGATT

ATATGAAATTATGTTTTCTTGCTTTATATAACACTATTAATGAAATTGCTTATGATAACTTAAAAGATAA

AGGTGAAAATATTTTACCATATTTAACAAAAGCTTGGGCTGATTTATGTAATGCTTTTTTACAAGAAGCT

AAATGGTTATATAATAAATCAACACCAACATTTGATGATTATTTTGGTAATGCTTGGAAAAGTTCATCTG

GTCCATTACAATTAGTTTTTGCTTATTTTGCTGTTGTTCAAAATATTAAAAAAGAAGAAATTGAAAATTT

ACAAAAATATCATGATACAATTTCACGTCCATCACATATTTTTCGTTTATGTAATGATTTAGCTTCAGCT

TCAGCTGAAATTGCACGTGGTGAAACAGCAAATTCAGTTTCATGTTATATGCGTACAAAAGGTATTTCTG

AAGAATTAGCTACAGAATCAGTTATGAATTTAATTGATGAAACATGGAAAAAAATGAATAAAGAAAAATT

AGGTGGTTCTTTATTTGCTAAACCATTTGTTGAAACTGCTATTAATTTAGCACGTCAATCACATTGTACT

TATCATAATGGTGATGCTCATACATCACCAGATGAATTAACACGTAAACGTGTTTTATCAGTTATTACAG

AACCAATTTTACCATTTGAACGTTAA
```

SEQ ID NO: 4 Polypeptide sequence for Cr-IspS isoprene synthase gene. The three copies of the hemagglutinin HA tag are underlined. The isoprene synthase sequence lacks a chloroplast targeting sequence of the poplar IspS protein sequence. The IspS sequence starts with "CS . . .", indicated by the change of font.

```
M<u>YPYDVPDYAG</u><u>YPYDVPDYAG</u><u>YPYDVPDYA</u>GPWCSVSTENVSFTETETEARRSANYEPNSWDYDY

LLSSDTDESIEVYKDKAKKLEAEVRREINNEKAEFLTLLELIDNVQRLGLGYRFESDIRGALDRFVSSGG

FDAVTKTSLHGTALSFRLLRQHGFEVSQEAFSGFKDQNGNFLENLKEDIKAILSLYEASFLALEGENILD

EAKVFAISHLKELSEEKIGKELAEQVNHALELPLHRRTQRLEAVWSIEAYRKKEDANQVLLELAILDYNM

IQSVYQRDLRETSRWWRRVGLATKLHFARDRLIESFYWAVGVAFEPQYSDCRNSVAKMFSFVTIIDDIYD

VYGTLDELELFTDAVERWDVNAINDLPDYMKLCFLALYNTINEIAYDNLKDKGENILPYLTKAWADLCNA

FLQEAKWLYNKSTPTFDDYFGNAWKSSSGPLQLVFAYFAVVQNIKKEEIENLQKYHDTISRPSHIFRLCN

DLASASAEIARGETANSVSCYMRTKGISEELATESVMNLIDETWKKMNKEKLGGSLFAKPFVETAINLAR

QSHCTYHNGDAHTSPDELTRKRVLSVITEPILPFER
```

SEQ ID NO: 5 Nucleotide sequence of Ss-IspS DNA and plasmid pIspS for cyanobacteria The first underlined sequence of SEQ ID NO:5 represents the (reverse complement) beta-lactamase gene, whereas the second underlined sequence is the Ss-IspS DNA. Additionally, the italicized sequences are start and stop codons, and the bold sequences are cloning restriction sites.
>pIspS

```
aaaaagcattgctcatcaatttgttgcaacgaacaggtcactatcagtcaaaataaaatcattatttaaaagggg cccgagcttaagactggccgtcgttttacaacacagaaagagtttgtagaaacgcaaaaaggccatccgtcaggg gccttctgcttagtttgatgcctggcagttccctactctcgccttccgcttcctcgctcactgactcgctgcgct cggtcgttcggctgcggcgagcggtatcagctcactcaaaggcggtaatacggttatccacagaatcaggggata acgcaggaaagaacatgtgagcaaaaggccagcaaaaggccaggaaccgtaaaaaggccgcgttgctggcgtttt tccataggctccgcccccctgacgagcatcacaaaaatcgacgctcaagtcagaggtggcgaaacccgacaggac tataaagataccaggcgtttccccctggaagctccctcgtgcgctctcctgttccgaccctgccgcttaccggat acctgtccgcctttctcccttcgggaagcgtggcgctttctcatagctcacgctgtaggtatctcagttcggtgt aggtcgttcgctccaagctgggctgtgtgcacgaaccccccgttcagcccgaccgctgcgccttatccggtaact atcgtcttgagtccaacccggtaagacacgacttatcgccactggcagcagccactggtaacaggattagcagag cgaggtatgtaggcggtgctacagagttcttgaagtggtgggctaactacggctacactagaagaacagtatttg
```

-continued gtatctgcgctctgctgaagccagttaccttcggaaaaagagttggtagctcttgatccggcaaacaaaccaccg ctggtagcggtggttttttttgtttgcaagcagcagattacgcgcagaaaaaaggatctcaagaagatcctttga tcttttctacggggtctgacgctcagtggaacgacgcgcgcgtaactcacgttaagggattttggtcatgagctt gcgccgtcccgtcaagtcagcgtaatgctctgc*ttaccaatgcttaatcagtgaggcacctatctcagcgatctg*

*tctatttcgttcatccatagttgcctgactccccgtcgtgtagataactacgatacgggagggcttaccatctgg*

*ccccagcgctgcgatgataccgcgagaaccacgctcaccggctccggatttatcagcaataaaccagccagccgg*

*aagggccgagcgcagaagtggtcctgcaactttatccgcctccatccagtctattaattgttgccgggaagctag*

*agtaagtagttcgccagttaatagtttgcgcaacgttgttgccatcgctacaggcatcgtggtgtcacgctcgtc*

*gtttggtatggcttcattcagctccggttcccaacgatcaaggcgagttacatgatcccccatgttgtgcaaaaa*

*agcggttagctccttcggtcctccgatcgttgtcagaagtaagttggccgcagtgttatcactcatggttatggc*

*agcactgcataattctcttactgtcatgccatccgtaagatgcttttctgtgactggtgagtactcaaccaagtc*

*attctgagaatagtgtatgcggcgaccgagttgctcttgcccggcgtcaatacgggataataccgcgccacatag*

*cagaactttaaaagtgctcatcattggaaaacgttcttcggggcgaaaactctcaaggatcttaccgctgttgag*

*atccagttcgatgtaacccactcgtgcacccaactgatcttcagcatcttttactttcaccagcgtttctgggtg*

*agcaaaaacaggaaggcaaaatgccgcaaaaaagggaataagggcgacacggaaatgttgaatactcat*attctt ccttttcaatattattgaagcatttatcagggttattgtctcatgagcggatacatatttgaatgtatttagaa aaataaacaaataggggtcagtgttacaaccaattaaccaattctgaacattatcgcgagcccatttatacctga atatggctcataacaccccttgcagtgcgactaacggcatgaagctcgtcggggaaataatgatttttattttgac tgatagtgacctgttcgttgcaacaaattgataagcaatgctttcttataatgccaactttgtacaagaaagctg ggtccatggaagctcgacgaagcgctaattatgaaccaaatagttgggactacgattttctattatcctctgata

*cggatgagtccattgaagtttataaggataaagctaagaaattggaagccgaagtgcgccgcgaaattaacaatg*

*agaaagcggaattttttgaccttattagaactcatcgataatgtgcaacgactgggattgggctatcggtttgaaa*

*gtgacatccgccgggcactggatcgttttgtatctagtggcggctttgatggcgtcactaaaactagtttgcacg*

*cgaccgcactcagttttcggctattacgtcaacacggtttcgaagtgagtcaagaggcgtttagtggcttcaaag*

*atcaaaatggcaattttctggaaaacttgaaagaagacacaaaagctatcctaagtttatacgaagctagttttc*

*tcgcgctggaaggtgaaaatattctggatgaggctcgtgtatttgcaatttctcacctgaaagaattatctgaag*

*aaaagattggcaaagaactcgccgaacaggtaaatcacgccttggaactgcccctccatcgtcgtacccaacgat*

*tggaagctgtgtggagtatcgaagcctatcgcaagaaagaagacgctaaccaagttttgttggaactggccatct*

*tggattataacatgattcaatccgtatatcagcgcgatctacgtgaaacgtctcggtggtggcggcgtgttgggc*

*tcgctactaaattacattttgcaaaggatcgactcattgaatcctttttattgggccgtcgggtggcttttgaac*

*cccagtacagcgattgccgtaattctgtagcaaaaatgttttctttcgttacaattattgatgacatttatgacg*

*tttacggcacctcgacgaactggaattgttcactgacgctgtggaacgttgggacgtaaatgccattaatgacc*

*tgccagattacatgaagttgtgttttctcgcgttatataacaccattaatgaaattgcatacgacaatttaaagg*

*ataagggagagaatattctgccttatttgacgaaagcctgggccgatttgtgtaatgccttttttgcaggaagcta*

*aatggttatataacaaatccaccccccacttttgatgactattttggcaatgcctggaagagcagcagcgggcctc*

*tccaactgattttttgcttattttgcggtagtacaaaacattaagaaagaagagattgaaaatttgcaaaagtacc*

*atgacattattagtcggcccagtcatattttccgcttgtgcaacgacctggcatccgctagtgccgaaattgcgc*

*gtggcgaaacagctaatagtgtgagttgttacatgcgcacaaagggcatttccgaagaactagctacggaaagtg*

*tcatgaacctgattgacgagacttgcaagaaaatgaataaggaaaaattgggcgggtccctatttgccaaaccct*

-continued ttgtggaaaccgcgattaatttggctcgccaaagtcattgtacctatcacaatggtgatgctcacaccagtcccg atgaattaacccgtaaacgagttctgtctgtgattactgaacccattttgcccttttgaacgttaaaagtaacagg ttttccatgttgtcgtctgcaagaacactgcagagcctgcttttttgtacaaagttggcattata SEQ ID NO:6 Amino acid sequence of the expected 65kD translated Ss-IspS protein from cyanobacteria plasmid.
```
  1 MEARRSANYE PNSWDYDFLL SSDTDESIEV YKDKAKKLEA EVRREINNEK

51 AEFLTLLELI DNVQRLGLGY RFESDIRRAL DRFVSSGGFD GVTKTSLHAT

101 ALSFRLLRQH GFEVSQEAFS GFKDQNGNFL ENLKEDTKAI LSLYEASFLA

151 LEGENILDEA RVFAISHLKE LSEEKIGKEL AEQVNHALEL PLHRRTQRLE

201 AVWSIEAYRK KEDANQVLLE LAILDYNMIQ SVYQRDLRET SRWWRRVGLA

251 TKLHFAKDRL IESFYWAVGV AFEPQYSDCR NSVAKMFSFV TIIDDIYDVY

301 GTLDELELFT DAVERWDVNA INDLPDYMKL CFLALYNTIN EIAYDNLKDK

351 GENILPYLTK AWADLCNAFL QEAKWLYNKS TPTFDDYFGN AWKSSSGPLQ

401 LIFAYFAVVQ NIKKEEIENL QKYHDIISRP SHIFRLCNDL ASASAEIARG

451 ETANSVSCYM RTKGISEELA TESVMNLIDE TCKKMNKEKL GGSLFAKPFV

501 ETAINLARQS HCTYHNGDAH TSPDELTRKR VLSVITEPIL PFER*
```

SEQ ID NO:7 *Pueraria montana* var. lobata (kudzu vine) isoprene synthase (IspS); ACCESSION No AY316691 (complete cds.) The atg start codon is underlined and indicates the start of the protein-coding region of the cDNA.
```
   1 aatcaatata taatatttac ggaagatttg atgcctttcc tgattttaat ttatttttat 61 ccctgcataa aataattgtg gtcaccgtac actgttcttg tcacttggac aagaaatttg 121 actagcaagc aaggtataat cattcatcta aacttatggt gatttattgc cccacctcat 181 caattttcgt gtgttttatt ttagtgtcct tggatcctcg ttccaatata aaggagaac 241 atggcatcgc aattttagag catatcattg aaaagtc_atg_ gcaaccaacc ttttatgctt 301 gtctaataaa ttatcgtccc ccacaccaac accaagtact agatttccac aaagtaagaa 361 cttcatcaca caaaaaacat ctcttgccaa tcccaaacct tggcgagtta tttgtgctac 421 gagctctcaa tttacccaaa taacagaaca taatagtcgg cgttcagcta attaccagcc 481 aaacctctgg aattttgaat ttctgcagtc tctggaaaat gaccttaagg tgattataca 541 tatattccag ttaattttc tttttttctt ttgtgatttt taaggaatca tttagtttgg 601 gaaagtatt ttttatttg cacttttaat tataaaaatg ttatatcatt ttcacttttt 661 tctattcatt tcaaaatt tacatagaaa acagtaaatt tttattttt tttatttct 721 attttcatta tttctcaaat caaacggtat taaagcataa acaaagaaat taatattgtt 781 cttttaattt tatttttta caataatggg aacgattata tattaggctg accttaataa 841 gttattttt ttttataata ttgttcttat tgtaacctaa cgacaggtgg aaaaactaga 901 agagaaggca acaaagctag aggaggaggt acgatgcatg atcaacagag tagacacaca 961 accattaagc ttactagaat tgatcgacga tgtccagcgt ctaggattga cctacaagtt 1021 tgagaaggac ataatcaaag cccttgagaa tattgttttg ctggatgaga ataagaaaaa 1081 taaaagtgac ctccatgcta ctgctctcag cttccgttta cttagacaac atggctttga 1141 ggtttcccaa ggtatttatg tatatatatg ttacccactt agcaacatat atatatatat 1201 atattatgat tcactgacca tgcatgtggt gcagatgtgt tgagagatt taaggacaag 1261 gagggaggtt tcagtggtga acttaaaggt gatgtgcaag ggttgctgag tctatatgaa 1321 gcatcctatc ttggctttga gggagaaaat ctcttggagg aggcaaggac attttcaata
```

```
1381 acacatctca agaacaacct aaaagaagga ataaacacca aagtggcaga acaagttagt 1441 catgcactgg aacttcccta tcatcaaaga ttgcatagac tagaagcacg atggttcctt 1501 gacaaatatg aaccaaagga accccaccat cagttactac tcgagcttgc aaagctagat 1561 ttcaatatgg tgcaaacatt gcaccagaaa gaactgcaag acctgtcaag gttagaaatt 1621 tcaattctca agtaattatt acctcataag aaattaaata acaataacaa tattgagtgt 1681 agagatttcc aattaaaaat taacatacga gaggatcaat atatattctt aggtatgtgg 1741 tactaatgaa atatatgcta ggtggtggac ggagatgggg ctagcaagca agctagactt 1801 tgtccgagac agattaatgg aagtgtattt ttgggcgttg ggaatggcac ctgatcctca 1861 attcggtgaa tgtcgtaaag ctgtcactaa aatgtttgga ttggtcacca tcatcgatga 1921 tgtatatgac gtttatggta ctttggatga gctacaactc ttcactgatg ctgttgagag 1981 gttcgtaatt gatttcagtc tcgattcagt tggaatttaa ttattgctta attaataata 2041 acttgcgtac atgcatacac acagatggga cgtgaatgcc ataaacacac ttccagacta 2101 catgaagttg tgcttcctag cactttataa caccgtcaat gacacgtctt atagcatcct 2161 taaagaaaaa ggacacaaca acctttccta tttgacaaaa tctgtacata tatactaatt 2221 atctccttgg ttgattaatt agtttagttt agtttagttg gtatgtcaac acaattaatt 2281 aatattatat atggatgttg acagtggcgt gagttatgca aagcattcct tcaagaagca 2341 aaatggtcga acaacaaaat cattccagca tttagcaagt acctgaaaaa tgcatcggtg 2401 tcctcctccg gtgtggcttt gcttgctcct tcctacttct cagtgtgcca acaacaagaa 2461 gatatctcag accatgctct tcgttctta actgatttcc atggccttgt gcgctcctca 2521 tgcgtcattt tcagactctg caatgatttg gctacctcag cggtgtgtaa ttaattacct 2581 taattaattt gtaacacttg ttagactaat atatataggt gtgtctgtta attactacag 2641 gctgagctag agaggggtga gacgacaaat tcaataatat cttatatgca tgagaatgac 2701 ggcacttctg aagagcaagc acgtgaggag ttgagaaaat tgatcgatgc agagtggaag 2761 aagatgaacc gagagcgagt ttcagattct acactactcc caaaagcttt tatggaaata 2821 gctgttaaca tggctcgagt ttcgcattgc acataccaat atggagacgg acttggaagg 2881 ccagactacg ccacagagaa tagaatcaag ttgctactta tagacccctt tccaatcaat 2941 caactaatgt acgtgtaaca acacaatata aacacttttc tacaagtata tatttgttta 3001 atttcggtgt tgaattaggg gtcaacacag atatatatac ttcaatggac caactcaacc 3061 aatctgataa gagaaaaaaa ataaaaataa ggttaggtta actttgtata aatccaagtt 3121 agatatcaag ttt
```

SEQ ID NO:8 *Pueraria montana* var. lobata (kudzu vine) isoprene synthase polypeptide sequence

MATNLLCLSNKLSSPTPTPSTRFPQSKNFITQKTSLANPKPWRVICATSSQFTQITEHNSRRSANYQPNL

WNFEFLQSLENDLKVEKLEEKATKLEEEVRCMINRVDTQPLSLLELIDDVQRLGLTYKFEKDIIKALENI

VLLDENKKNKSDLHATALSFRLLRQHGFEVSQDVFERFKDKEGGFSGELKGDVQGLLSLYEASYLGFEGE

NLLEEARTFSITHLKNNLKEGINTKVAEQVSHALELPYHQRLHRLEARWFLDKYEPKEPHHQLLLELAKL

DFNMVQTLHQKELQDLSRWWTEMGLASKLDFVRDRLMEVYFWALGMAPDPQFGECRKAVTKMFGLVTIID

DVYDVYGTLDELQLFTDAVERWDVNAINTLPDYMKLCFLALYNTVNDTSYSILKEKGHNNLSYLTKSWRE

LCKAFLQEAKWSNNKIIPAFSKYLENASVSSSGVALLAPSYFSVCQQQEDISDHALRSLTDFHGLVRSSC

VIFRLCNDLATSAAELERGETTNSIISYMHENDGTSEEQAREELRKLIDAEWKKMNRERVSDSTLLPKAF

MEIAVNMARVSHCTYQYGDGLGRPDYATENRIKLLLIDPFPINQLMYV

What is claimed is:

1. A method of producing isoprene hydrocarbons in a green microalgae, the method comprising:
   introducing an expression cassette that comprises a nucleic acid encoding an isoprene synthase that comprises amino acid residues 53-595 of SEQ ID NO:2 into the chloroplast or nuclear genome of the green microalgae, wherein the nucleic acid is codon-optimized for expression in the green microalgae and comprises at least 95% identity to the isoprene synthase coding region of SEQ ID NO:3; and
   culturing the green microalgae under conditions in which the nucleic acid encoding isoprene synthase is expressed and produces isoprene.

2. The method of claim 1, wherein the green microalgae is selected from the group consisting of *Chlamydomonas reinhardtii, Scenedesmus obliquus, Chlorella vulgaris* and *Dunaliella salina*.

3. The method of claim 1, wherein the nucleic acid comprises the isoprene synthase coding region of SEQ ID NO:3.

4. A method of producing isoprene hydrocarbons in a green microalgae that comprises a heterologous nucleic acid in the chloroplast or nuclear genome that encodes isoprene synthase, the method comprising:
   mass-culturing a green microalgae in an enclosed bioreactor under conditions in which the isoprene synthase gene is expressed and produces isoprene,
   wherein the green microalgae comprises a heterologous nucleic acid encoding an isoprene synthase in the chloroplast or nuclear genome, wherein the heterologous nucleic acid encodes amino acid residues 53-595 of SEQ ID NO:2 and the nucleic acid: (i) is codon-optimized for expression in the green microalgae and (2) comprises at least 95% identity to the isoprene synthase coding region of SEQ ID NO:3; and
   harvesting volatile isoprene hydrocarbons produced by the green microalgae.

5. The method of claim 4, wherein the green microalgae is selected from the group consisting of *Chlamydomonas reinhardtii, Scenedesmus obliquus, Chlorella vulgaris* and *Dunaliella salina*.

6. The method of claim 4, wherein the heterologous nucleic acid comprises the isoprene synthase coding region of SEQ ID NO:3.

7. The method of claim 1, wherein the nucleic acid comprises at least 97% identity to the isoprene synthase coding region of SEQ ID NO:3.

8. The method of claim 4, wherein the nucleic acid comprises at least 97% identity to the isoprene synthase coding region of SEQ ID NO:3.

* * * * *